(12) United States Patent
Paczesny

(10) Patent No.: US 11,193,945 B2
(45) Date of Patent: Dec. 7, 2021

(54) METHODS FOR DETECTING SINUSOIDAL OBSTRUCTIVE SYNDROME (SOS)

(71) Applicant: INDIANA UNIVERSITY RESEARCH AND TECHNOLOGY CORPORATION, Indianapolis, IN (US)

(72) Inventor: Sophie Paczesny, Indianapolis, IN (US)

(73) Assignee: Indiana Research and Technology Corporation, Indianapolis, IN (US)

(*) Notice: Subject to any disclaimer, the term of this patent is extended or adjusted under 35 U.S.C. 154(b) by 0 days.

(21) Appl. No.: 16/781,407

(22) Filed: Feb. 4, 2020

(65) Prior Publication Data

US 2020/0182886 A1 Jun. 11, 2020

Related U.S. Application Data

(63) Continuation of application No. 15/521,783, filed as application No. PCT/US2015/057393 on Oct. 26, 2015, now abandoned.

(60) Provisional application No. 62/069,394, filed on Oct. 28, 2014.

(51) Int. Cl.

| | |
|---|---|
| *G01N 33/53* | (2006.01) |
| *G01N 33/577* | (2006.01) |
| *G01N 33/68* | (2006.01) |
| *C07K 14/715* | (2006.01) |
| *C07K 14/78* | (2006.01) |
| *C07K 14/705* | (2006.01) |
| *C07K 16/18* | (2006.01) |
| *C07K 16/28* | (2006.01) |
| *A61B 5/145* | (2006.01) |
| *G01N 30/72* | (2006.01) |

(52) U.S. Cl.
CPC ...... *G01N 33/6893* (2013.01); *A61B 5/14546* (2013.01); *C07K 14/7056* (2013.01); *C07K 14/70542* (2013.01); *C07K 14/7155* (2013.01); *C07K 14/78* (2013.01); *C07K 16/2836* (2013.01); *C07K 16/2851* (2013.01); *G01N 30/72* (2013.01); *G01N 33/53* (2013.01); *G01N 33/577* (2013.01); *G01N 33/68* (2013.01); *G01N 2333/4724* (2013.01); *G01N 2333/70503* (2013.01); *G01N 2333/78* (2013.01); *G01N 2400/40* (2013.01); *G01N 2800/08* (2013.01); *G01N 2800/085* (2013.01); *G01N 2800/245* (2013.01); *G01N 2800/52* (2013.01)

(58) Field of Classification Search
CPC ........ G01N 2800/52; G01N 2800/245; G01N 2800/08; G01N 2800/085; G01N 33/53; G01N 33/577; G01N 33/68; G01N 33/6893; G01N 2333/70503; G01N 2333/78; G01N 2333/7155; G01N 2333/4724; G01N 2400/40; C07K 14/7155; C07K 14/78; C07K 14/4726; C07K 14/70542; C07K 14/7056; C07K 16/28; C07K 16/2851; C07K 16/2836

See application file for complete search history.

(56) References Cited

U.S. PATENT DOCUMENTS

2011/0287964 A1   11/2011   Bonventre et al.

FOREIGN PATENT DOCUMENTS

CN   102858985   1/2013

OTHER PUBLICATIONS

Fulgenzi et al. Defibrotide in the treatment of hepatic veno-occlusive disease. Hepatic Med Evidence Res 8: 105-113, 2016.*
Richardson et al. Systemic review of defibrotide studies in the treatment of veno-occlusive disease/sinusoidal obstruction syndrome (VOD/SOS). Bone Marrow Transplant 54: 1951-1962, 2019.*
Paczesny et al. Translational research efforts in biomarkers and biology of early transplant-related complications. Biol Blood Marrow Transplant 17(1): S101-S108, 2011.
Bearman et al., "Venoocclusive disease of the liver: development of a model for predicting fatal outcome after marrow transplantation," J Clin Oneal_ 1993: 11(9), pp. 1729-1736.
Faca et al., "Quantitative analysis of acrylamide labeled serum proteins by LC-MS/MS," J_ Proteome Res_ 2006: 5(8): pp. 2009-2018_.
Faca et al., "Contribution of protein fractionation to depth of analysis of the serum and plasma proteomes," J Proteome Res_ 2007: 6(9), pp. 3558-3565_.
Hu et al, Early Increased Ficolin-2 Concentrations are Associated with Severity of Liver Inflammation and Efficacy of anti-Viral Therapy in Chronic Hepatitis C Patients, Scandinavian Journal of Immunology_ Feb. 2013, vol. 77, No. 2 pp. 144-150.
Jones et al_ "Venoocclusive disease of the liver following bone marrow transplantation," Transplantation, 1987: 44(6), pp. 778-783.
Paczesny et al, "Elafin is a biomarker of graft-versus-host disease of the skin," Science Translational Medicine, 2010: 2(13), pp. 13ra12.
Rahbari et al., Hyaluronic Acid as a Marker of Sinusoidal Obstruction Syndrome after Oxaliplatin-based Chemotherapy for Colorectal Liver Metastases; Don't Forget the Tumor_ Annals of Surgical Oncology, May 2013, vol. 20. No 5, pp. 1405-1407.

(Continued)

*Primary Examiner* — Bridget E Bunner
(74) *Attorney, Agent, or Firm* — Barnes & Thornburg LLP

(57) ABSTRACT

Disclosed are biomarker panels for evaluating subjects at risk of sinusoidal obstruction syndrome (SOS) early after hematopoietic stem cell transplantation (HSCT). In particular, the present disclosure relates to the use of one or more of ST2, ANG2, L-Ficolin, HA, and VCAM1 for prognosing, diagnosing, and/or treating SOS.

6 Claims, 9 Drawing Sheets

(56) References Cited

OTHER PUBLICATIONS

Richardson et al, Hepatic Veno-Occlusive Disease after Hematopoietic Stem Cell Transplantation: Novel Insights to Pathogenesis, Current Status of Treatment, and Future Directions. Biology Blood Marrow Transplant, Jan. 2013, vol. 19, Suppl 1, pp. S88-S90.

UEDA et at, Predictive Value of Circulating Angiopoietin-2 for Endothelial Damage-Related Complications 1n Allogenic Hematopoietic Stem Cell Transplantation_ Biology of Blood and Marrow Transplantation, Sep. 2014, vol. 20, No. 9 pp. 1335-1340.

Shulman et al., "Hepatic veno-occlusion disease—liver toxicity syndrome after bone marrow transplantation," Bone Marrow Transplant 1992: 10(3):197-214.

Akil et al., Biomarkers for Diagnosis and Prognosis of Sinusoidal Obstruction Syndrome after Hematopoietic Cell Transplantation; Biology of Blood and Marrow Transplantation; 2015; pp. 1739-1745.

Fried et al., Serum hyaluronic acid in patients with veno-occlusive disease following bone marrow transplantation; Bone Marrow Transplantation; 2001, vol. 27, pp. 635-639.

Holtan et al., Acute graft-versus-host disease: a bench-to-bedside update; Advances in Hematopoietic Cell Transplantation; 2014, vol. 124, No. 3, pp. 363-373.

Lee et al_, Plasminogen activator inhibitor-1 is an independent diagnostic marker as well as severity predictor of hepatic veno-occlusive disease after allogeneic bone marrow transplantation in adults conditioned with busulphan and cyclophosphamide; British Journal of Haemetology; 2002, vol. 118, pp. 1087-1094._.

Tanikawa et al., Predictive markers for hepatic veno-occlusive disease after hematopoietic stem cell transplantation n adults: a prospective single center study; 2000, vol. 26, pp. 881-886.

* cited by examiner

METHODS FOR DETECTING SINUSOIDAL OBSTRUCTIVE SYNDROME (SOS)

CROSS-REFERENCE TO RELATED APPLICATIONS

This application is a continuation of U.S. application Ser. No. 15/521,783, filed on Apr. 25, 2017, which is a U.S. national counterpart application of international application serial No. PCT/US2015/057393 filed Oct. 26, 2015, which claims priority to U.S. Provisional Application Ser. No. 62/069,394, filed Oct. 28, 2014, which is hereby incorporated by reference in its entirety.

STATEMENT REGARDING FEDERALLY SPONSORED RESEARCH & DEVELOPMENT

This invention was made with government support under HD071598, HL101102, and CA168814 awarded by the National Institutes of Health. The government has certain rights in the invention.

FIELD OF THE DISCLOSURE

The present disclosure relates generally to biomarkers for evaluating subjects at risk of sinusoidal obstruction syndrome (SOS) early after hematopoietic stem cell transplantation (HSCT). In particular, the present disclosure relates to the use of ST2, ANG2, L-Ficolin, HA, and VCAM1 as a biomarker panel for prognosing, diagnosing, and/or treating SOS (also referred to as veno-occlusive disease (VOD)). The present disclosure is further directed to the use of this biomarker panel for preemptive intervention to minimize the incidence and severity of SOS.

BACKGROUND OF THE DISCLOSURE

Hematopoietic stem cell transplantation (HSCT) is a potentially life-saving treatment for many patients with inherited disorders and hematologic malignancies. However, its practical use is impeded by the risk of serious adverse events, including sinusoidal obstruction syndrome (SOS, the now preferred name for veno-occlusive disease (VOD), occurring after stem cell transplantation or chemotherapy). Although the overall incidence and severity has fallen in the recent years, SOS is still a life-threatening liver injury complication with greater than 80% mortality in severe cases that affects up to 20% of allogeneic HSCT recipients in some centers. SOS can also occur after intense chemotherapy when either the chemotherapy or radiation induces both systemic inflammation and tissue damage particularly to the sinusoidal endothelial cells of the hepatic acinus. In addition, SOS can also occur after use of drugs such as gemtuzumab ozogamicin and the combination of tacrolimus and sirolimus under certain circumstances.

The pathogenesis of SOS is complex, involving cytokine release, endothelial injury, hemostatic activation, and hepatic drug detoxification through the glutathione pathway. Hepatocellular necrosis, fibrosis, and vascular occlusion ultimately lead to liver failure, hepatorenal syndrome, multiorgan failure, and death. Patients with SOS may present with the classical triad of unexplained weight gain and ascites and, in more severe cases, respiratory distress due to fluid overload, elevated bilirubin, and right upper quadrant pain in severe cases. However, the presentation may be variable in less severe cases. Thus, the etiology of abdominal pain and weight gain following HSCT presents a diagnostic challenge. SOS typically occurs between the first and third weeks after HSCT, but may occur later, and is often clinically indistinguishable from other causes of weight gain and respiratory distress particularly in children (e.g., cytokine storm syndrome and idiopathic pneumonia syndrome) or other causes of abdominal pain and jaundice (e.g., graft-versus-host disease of the gastrointestinal tract or liver). Diagnosis of SOS is assessed according to two clinical scales (Baltimore (Jones R J et al., "Venoocclusive disease of the liver following bone marrow transplantation," Transplantation, 1987: 44(6):778-783) and Seattle (Shulman H M et al., "Hepatic veno-occlusion disease—liver toxicity syndrome after bone marrow transplantation," Bone Marrow Transplant. 1992: 10(3):197-214)) that measures different degrees of liver dysfunction and weight gain, and abdominal ultrasound, showing a reversal of the sinusoidal flow, is commonly used to confirm the diagnosis. However, these clinical criteria and reversal of the sinusoidal flow are late events in the pathology of the disease, and ultrasound examination for this phenomenon is not standardized and varies according to operator-dependent practices. Histological evaluation is not routinely performed to confirm the diagnosis in these patients due to their increased risk for bleeding complications with liver biopsy.

Although there is general agreement on the use of clinical criteria for diagnosing SOS, no definitive consensus has been reached regarding a suitable classification system for disease severity beyond the Bearman scale (Bearman S I et al., "Venoocclusive disease of the liver: development of a model for predicting fatal outcome after marrow transplantation," J Clin Oncol. 1993: 11(9):1729-1736). Consequently, a diagnosis of severe SOS is associated with multiorgan failure and a high mortality rate.

Although no agents have been approved for SOS treatment in the United States, the investigational drug defibrotide has shown the most promising results in several clinical trials and is approved in the European Union for treatment of SOS. Defibrotide is a polydisperse oligonucleotide with fibrinolytic properties and protective effects on vascular endothelium. However, treatment with defibrotide therapy carries significant risks when given late in the disease course, particularly severe hemorrhage. Therefore, a noninvasive method for early and accurate diagnosis of SOS is urgently needed.

Further, although a few potential biomarkers for SOS have been identified based on hypothesis-driven testing, there is still no validated blood test for SOS. Accordingly, there exists a need to identify non-invasive biomarkers for use in diagnosing and prognosing SOS early after HSCT. It would further be advantageous if these methods can be used to provide preemptive intervention to minimize the incidence and severity of SOS.

BRIEF DESCRIPTION OF THE DISCLOSURE

In one aspect, the present disclosure is directed to a diagnostic biomarker panel comprising suppressor of tumorigenicity 2 (ST2), angiopoietin 2 (ANG2), L-Ficolin, hyaluronic acid (HA) and vascular cell adhesion molecule 1 (VCAM1).

In another aspect, the present disclosure is directed to a prognosis biomarker panel comprising L-Ficolin, hyaluronic acid (HA) and vascular cell adhesion molecule 1 (VCAM1).

In another aspect, the present disclosure is directed to a method of diagnosing or of aiding diagnosis of sinusoidal obstructive syndrome (SOS) in a subject receiving hematopoietic stem cell transplantation (HSCT). The method comprises measuring in a biological sample from the subject the expression of at least one biomarker selected from the group consisting of ST2, ANG2, L-Ficolin, HA, and VCAM1 by contacting the biological sample obtained from the subject with a specific binding agent that specifically binds to the biomarker, wherein the specific binding agent forms a complex with the biomarker; and detecting the agent-biomarker complex, thereby determining the biomarker expression level; wherein an elevated biomarker expression level compared to biomarker expression obtained from a biological sample obtained from a control is indicative of SOS.

In another aspect, the present disclosure is directed to a method of prognosing or of aiding prognosis of sinusoidal obstructive syndrome (SOS) in a subject receiving hematopoietic stem cell transplantation (HSCT). The method comprises: measuring in a biological sample from the subject the expression of at least one biomarker selected from the group consisting of ST2, ANG2, L-Ficolin, HA, and VCAM1 by contacting the biological sample obtained from the subject with a specific binding agent that specifically binds to the biomarker, wherein the specific binding agent forms a complex with the biomarker; and detecting the agent-biomarker complex, thereby determining the biomarker expression level; wherein an elevated biomarker expression level compared to biomarker expression obtained from a biological sample obtained from a control is indicative of a prognosis for shortened survival compared to median survival in a subject having SOS, and wherein a reduced biomarker expression level compared to biomarker expression obtained from a biological sample obtained from a control is indicative of a prognosis for increased survival compared to median survival in a subject having SOS.

DETAILED DESCRIPTION OF THE DISCLOSURE

Figure 1:
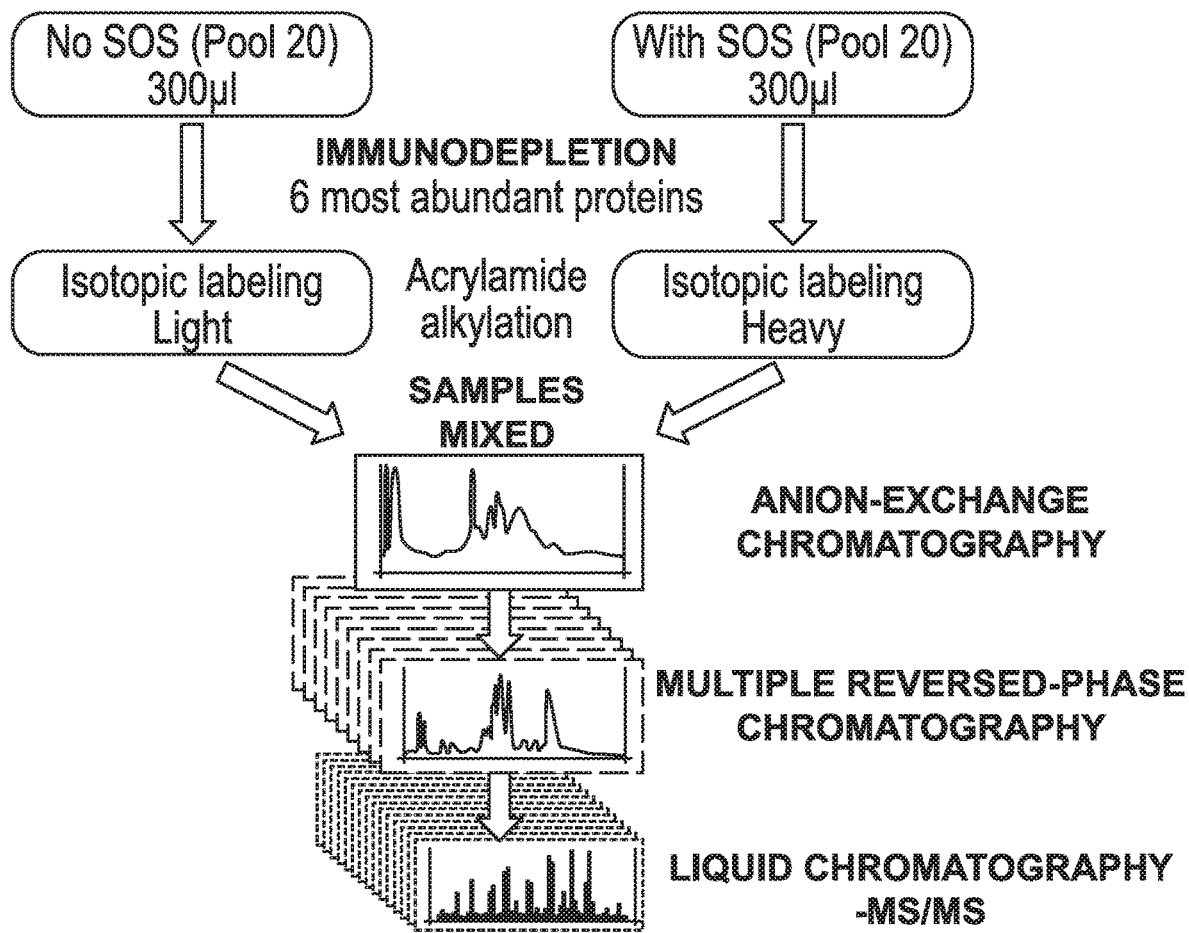
FIG. 1 depicts a flow diagram for the proteomics analysis used in the Examples below.
Figure 2A:
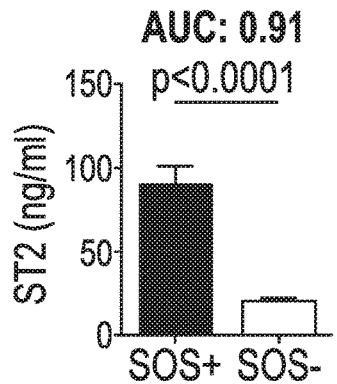
FIGS. 2A-2H depict eight diagnostic biomarkers of SOS according to the highest AUCs (0.91-0.70).
Figure 2B:
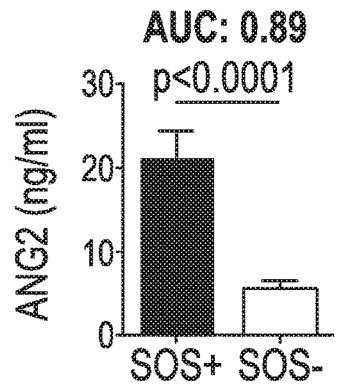
Figure 2C:
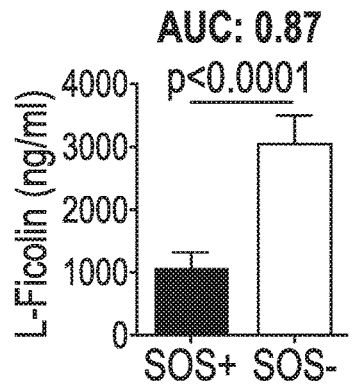
Figure 2D:
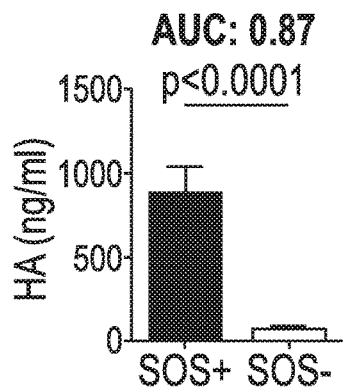
Figure 2E:
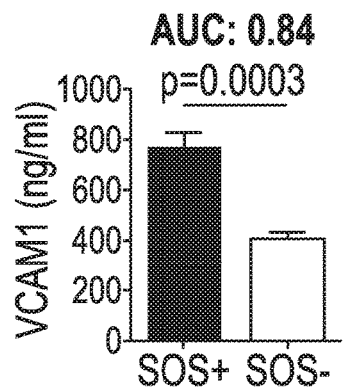
Figure 2F:
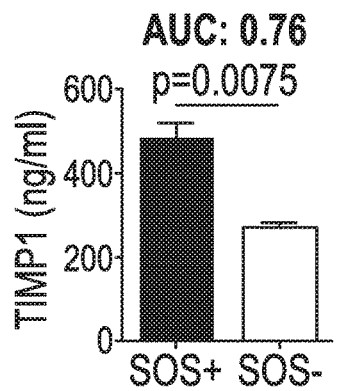
Figure 2G:
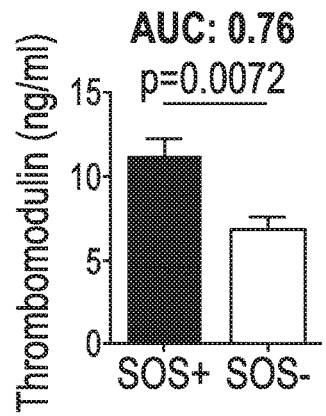
Figure 2H:
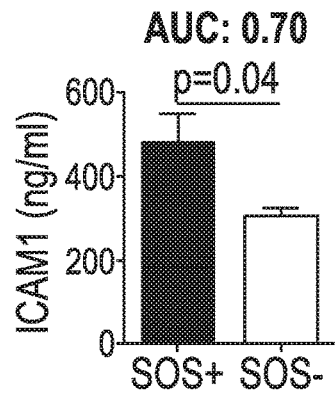

It has been discovered herein that suppressor of tumorigenicity 2 (ST2), angiopoietin 2 (ANG2), L-Ficolin, hyaluronic acid (HA) and vascular cell adhesion molecule 1 (VCAM1) can be employed in biomarker panels to diagnosis SOS. Further, in one embodiment, a biomarker panel can be employed to provide opportunities for preemptive intervention to minimize the incidence and severity of SOS clinical symptoms, and thereby increase survival. The present disclosure further relates to the use of these biomarkers and biomarker panels for prognosing, diagnosing, and/or treating SOS in a subject that has received or is receiving hematopoietic stem cell transplantation (HSCT).

The present disclosure uses examples to disclose the invention to enable any person skilled in the art to practice the invention, including making and using any panels or devices and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

Unless otherwise defined, all terms of art, notations and other scientific terminology used herein are intended to have the ordinary meanings commonly understood by those of ordinary skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

A. Definitions

As used herein, the term "biomarker" refers to an indicator of, for example, a pathological state of a subject, which can be detected in a biological sample of the subject. Biomarkers include DNA-based, RNA-based and protein-based molecular markers.

As used herein, the term "diagnosis" refers to the identification or classification of a molecular or pathological state, disease or condition. For example, "diagnosis" can refer to identification of a particular type of a condition (such as sinusoidal obstruction syndrome ("SOS")).

As used herein, the term "aiding diagnosis" refers to methods that assist in making a clinical determination regarding the presence, or nature, of a particular type of symptom of a condition (such as SOS). For example, a method of aiding diagnosis of a condition (such as SOS) can include measuring the expression of certain genes in a biological sample from an individual.

As used herein, the term "prognosis" is used herein to refer to the categorization of patients by degree of risk for a disease (such as SOS) or progression of such disease. A "prognostic marker" refers to an assay that categorizes patients by degree of risk for disease occurrence or progression.

As used herein, the term "sample" refers to a composition that is obtained or derived from a subject of interest that contains a cellular and/or other molecular entity that is to be characterized and/or identified, for example based on physical, biochemical, chemical and/or physiological characteristics. For example, the phrase "disease sample" and variations thereof refers to any sample obtained from a subject of interest that would be expected or is known to contain the cellular and/or molecular entity that is to be characterized. A "tissue" or "cell sample" refers to a collection of similar cells obtained from a tissue of a subject or patient. The source of the tissue or cell sample may be blood or any blood constituents (e.g., whole blood, plasma, serum) from the subject. The tissue sample can also be primary or cultured cells or cell lines. Optionally, the tissue or cell sample is obtained from a disease tissue/organ. The tissue sample can contain compounds which are not naturally intermixed with the tissue in nature such as preservatives, anticoagulants, buffers, fixatives, nutrients, antibiotics, and the like.

As used herein, the terms "control", "control cohort", "reference sample", "reference cell", "reference tissue", "control sample", "control cell", and "control tissue" refer to a sample, cell or tissue obtained from a source that is known, or believed, to not be afflicted with the disease or condition for which a method or composition of the invention is being used to identify. The control can include one control or multiple controls. In one embodiment, a reference sample, reference cell, reference tissue, control sample, control cell, or control tissue is obtained from a healthy part of the body of the same subject or patient in whom a disease or condition is being identified using a composition or method of the invention. In one embodiment, a reference sample, reference cell, reference tissue, control sample, control cell, or control tissue is obtained from a healthy part of the body of an individual who is not the subject or patient in whom a disease or condition is being identified using a composition or method of the invention.

The term "antibody" is used in its broadest sense and specifically covers, for example, monoclonal antibodies, polyclonal antibodies, antibodies with polyepitopic specificity, single chain antibodies, multi-specific antibodies and fragments of antibodies. Such antibodies can be chimeric, humanized, human and synthetic.

The term "subject" is used interchangeably herein with "patient" to refer to an individual to be treated. The subject is a mammal (e.g., human, non-human primate, rat, mouse, cow, horse, pig, sheep, goat, dog, cat, etc.). The subject can be a clinical patient, a clinical trial volunteer, an experimental animal, etc. The subject can be suspected of having or at risk for having a condition (such as SOS) or be diagnosed with a condition (such as SOS). The subject can also be suspected of having or at risk for having SOS. According to one embodiment, the subject to be treated according to this invention is a human.

As used herein, "treating", "treatment" and "alleviation" refer to measures, wherein the object is to prevent or slow down (lessen) the targeted pathologic condition or disorder or relieve some of the symptoms of the disorder. Those in need of treatment can include those already with the disorder as well as those prone to have the disorder, those at risk for having the disorder and those in whom the disorder is to be prevented.

"Elevated expression level" and "elevated levels" refer to an increased expression of a mRNA or a protein in a patient (e.g., a patient suspected of having or diagnosed as having SOS) relative to a control, such as subject or subjects who are not suffering from SOS.

B. Methods of Prognosing

In one embodiment, the present disclosure is directed to a method of prognosing or of aiding in the prognosis of sinusoidal obstructive syndrome (SOS) in a subject receiving hematopoietic stem cell transplantation (HSCT). The method comprises: obtaining a biological sample from the subject; measuring in a biological sample from the subject, the expression of at least one biomarker selected from the group consisting of ST2, ANG2, L-Ficolin, HA, and VCAM1 by contacting the biological sample obtained from the subject with a specific binding agent that specifically binds to the biomarker, wherein the specific binding agent forms a complex with the biomarker; and detecting the agent-biomarker complex, thereby determining the biomarker expression level; wherein an elevated biomarker expression level compared to biomarker expression obtained from a biological sample obtained from a control is indicative of a prognosis for shortened survival compared to median survival in a subject having SOS, and wherein a reduced biomarker expression level compared to biomarker expression obtained from a biological sample obtained from a control is indicative of a prognosis for increased survival compared to median survival in a subject having SOS.

The specific binding agent can be selected from a nucleic acid, an antibody, a receptor, and a lectin.

The sample can be selected from liver tissue, whole blood, plasma and serum.

In some embodiments, the step of measuring includes contacting the biological sample with a biomarker panel comprising L-Ficolin, hyaluronic acid (HA) and vascular cell adhesion molecule 1 (VCAM1).

The specific binding agent-biomarker complex can be detected using methods known to those skilled in the art such as, for example, microarray analysis, immunoassay, immunohistochemistry, and mass spectrometry. Representative immunoassays include Western blot analysis and ELISA.

It has been advantageously found that the biomarker panels used in the methods of the present disclosure can be used for prognosing SOS early after HSCT. Particularly, in some embodiments, the methods can be used to prognosis SOS the same day as HSCT. In other embodiments, prognosis can be made one week, two weeks, or three weeks from HSCT. Accordingly, the methods of prognosing SOS can include obtaining the biological sample at day 0 from HSCT, including obtaining the sample from day 0 to day 7 from HSCT, including obtaining the sample from day 0 to day 14 from HSCT, and including obtaining the sample from day 0 to day 21 from HSCT.

C. Methods of Diagnosing

In another embodiment, the present disclosure is directed to a method for diagnosing SOS in a subject, particularly a subject receiving hematopoietic stem cell transplantation (HSCT). The method comprises: measuring in a biological sample from the subject the expression of at least one biomarker selected from the group consisting of ST2, ANG2, L-Ficolin, HA, and VCAM1 by contacting the biological sample obtained from the subject with a specific binding agent that specifically binds to the biomarker, wherein the specific binding agent forms a complex with the biomarker; and detecting the agent-biomarker complex, thereby determining the biomarker expression level; wherein an elevated biomarker expression level compared to biomarker expression obtained from a biological sample obtained from a control is indicative of SOS.

The specific binding agent can be selected from a nucleic acid, an antibody, a receptor, and a lectin.

The sample can be selected from whole blood and plasma.

In some embodiments, the step of measuring includes contacting the biological sample with a biomarker panel comprising tumorigenicity 2 (ST2), angiopoietin 2 (ANG2), L-Ficolin, hyaluronic acid (HA) and vascular cell adhesion molecule 1 (VCAM1).

The specific binding agent-biomarker complex can be detected using methods known to those skilled in the art such as, for example, microarray analysis, immunoassay, immunohistochemistry, and mass spectrometry. Representative immunoassays include Western blot analysis and ELISA.

It has been advantageously found that the biomarker panels used in the methods of the present disclosure can be used for diagnosing SOS early after HSCT. Particularly, in some embodiments, the methods can be used to diagnose SOS the same day as HSCT. In other embodiments, diagnosis can be made one week, two weeks, or three weeks from HSCT. Accordingly, the methods of diagnosing SOS can include obtaining the biological sample at day 0 from HSCT, including obtaining the sample from day 0 to day 7 from HSCT, including obtaining the sample from day 0 to day 14 from HSCT, and including obtaining the sample from day 0 to day 21 from HSCT.

G. Biological Sample

The biological sample used in the methods of the present disclosure can be obtained using certain methods known to those skilled in the art. Biological samples may be obtained from vertebrate animals, and in particular, mammals. In certain instances, a biological sample is whole blood, plasma, or serum. By screening such body samples, a prognosis or diagnosis can be achieved for SOS.

As used in the various methods of the present disclosure, the terms "control", "control value", "reference" and "reference value" refer to an expression level value obtained from "control sample", "control cell", and "control tissue" "reference sample", "reference cell", and "reference tissue" obtained from a source that is known, or believed, to not be afflicted with the condition for which a method or composition is being used to identify. It is to be understood that the control need not be obtained at the same time as the biological sample of the subject is obtained. Thus, a control value for an expression level can be determined and used for comparison of the expression level for the biological sample of the subject or the biological samples of multiple subjects.

H. Detection of Biomarkers

Expression levels of proteins may be detected in samples of whole blood, plasma, or serum. Various methods are known in the art for detecting protein expression levels in such biological samples, including various immunoassay methods.

EXAMPLES

Materials and Methods
A. Patients and Samples

Three sets of HSCT patients were included in these Examples. Patients were treated at the University of Michigan, at Indiana University, and at University of Barcelona. All patients or their legal guardians provided written informed consent, and the study for post-HSCT complications samples collection was approved by the institutional review boards of the University of Michigan, Indiana University, and Hospital Clinic, University of Barcelona.

Heparinized blood samples were collected before or on the day of HCT, then weekly for 2 or 4 weeks after allogeneic HSCT, then monthly for 2 months, as well as at the time of key clinical events, including the onset of symptoms consistent with SOS. Plasma samples were collected prospectively per institutional guidelines.

For analysis, plasma samples were thawed and centrifuged at 12,000 rpm for 10 minutes to separate the clots at the bottom and lipids on top from the plasma. Then, 150-µl aliquots of each undiluted plasma sample were plated in 96-well V-bottom plates by manual pipetting. The plates were wrapped in parafilm and kept in a humid chamber at 4° C. during the entire process, which did not exceed 96 hours.

B. Proteomics Analysis

The methods used for sample preparation, protein fractionation, MS analysis, protein identification, and quantitative analysis of protein concentrations during the intact protein analysis system have been previously reported in Faca V. et al., "Quantitative analysis of acrylamide labeled serum proteins by LC-MS/MS," J. Proteome Res. 2006: 5(8):2009-2018; Faca V. et al., "Contribution of protein fractionation to depth of analysis of the serum and plasma proteomes," J Proteome Res. 2007: 6(9):3558-3565; and Paczesny S. et al., "Elafin is a biomarker of graft-versus-host disease of the skin," Science Translational Medicine, 2010: 2(13):13ra12. The MS-based proteomics approach used in these Examples is illustrated in FIG. 1.

C. Immunoassays

Suppressor of tumorigenicity 2 (ST2), angiopoietin2 (ANG2), L-Ficolin, hyaluronic acid (HA), vascular cell adhesion molecule 1 (VCAM1), tissue inhibitor of metalloproteinase 1 (TIMP1), thrombomodulin (sCD141), intercellular adhesion molecule 1 (ICAM1), plasminogen activator inhibitor-1 (PAI-1), von Willebrand factor (vWF), and CD97 concentrations were measured by enzyme-linked immunosorbent assays (ELISAs). The antibody pairs used for these ELISAs were as follows: anti-ST2 (R&D Systems, Minneapolis, Minn.), anti-ANG2 (R&D Systems), anti-L-Ficolin (Hycult Biotech, Plymouth Meeting, Pa.), anti-HA (Corgenix, Broomfield, Colo.), anti-VCAM1 (R&D Systems), anti-TIMP1 (R&D Systems), anti-thrombomodulin (Diaclone, Besancon, France), anti-ICAM1 (R&D Systems), anti-PAI-1 (eBioscience, San Diego, Calif.), anti-vWF (American Diagnostica, Stamford, Conn.), and anti-CD97 (R&D Systems).

Capture antibodies were reconstituted and diluted per manufacturers' specifications or pre-coated plates were used as recommended by the manufacturer. Then, 50-µl of diluted antibodies were added to wells of 96-well high-binding half-well plates, which were then sealed and incubated overnight. The next day, the test plates containing the capture antibodies were washed and blocked with specific manufacturer's recommended blocking buffer. After additional wash steps, 50-µl or 100-µl aliquots of plasma samples (dilutions listed in Table 1) were added in duplicate to the ELISA test plates. In addition, 50-µl or 100-µl aliquots of reconstituted standard at different concentrations (see Table 1) were added in duplicate for the preparation of 8-point standard curves per the manufacturers' protocols. After addition of samples and standard solutions, the plates were sealed and incubated for 2 hours at room temperature on a plate rotator at 300 rpm. The ELISAs were completed by adding biotinylated detection antibodies specific for each target followed by the enzyme horseradish peroxidase (HRP) and HRP substrate. The optical density of each well was read using a plate reader set to 450-570 nm. The ELISAs were performed in duplicate and sequentially.

TABLE 1

ELISA parameters for the 11 tested proteins

|  | Standard curve range | Dilution factor | CV % | LLOD (optical density) | LLOD (concentration) |
|---|---|---|---|---|---|
| ST2 | 2000-31 pg/ml | 1/50 | 3.30 | 0.06 | 6 pg/ml |
| ANG2 | 3000-47 pg/ml | 1/10 | 10.95 | 0.11 | 18 pg/ml |
| L-Ficolin | 1000-15 pg/ml | 1/100 | 2.90 | 0.04 | 7 pg/ml |
| HA | 800-50 ng/ml | NEAT | 2.67 | 0.06 | 9 ng/ml |
| VCAM | 1000-15 pg/ml | 1/2000 | 4.41 | 0.01 | 12 pg/ml |
| TIMP1 | 2000-31 pg/ml | 1/250 | 4.70 | 0.02 | 7 pg/ml |
| Thrombomodulin | 20-0.62 ng/ml | 1/4 | 6.60 | 0.21 | 0.50 ng/ml |
| ICAM | 2000-31 pg/ml | 1/500 | 0.93 | 0.03 | 23 pg/ml |
| PAI-1 | 5000-78 pg/ml | 1/100 | 3.60 | 0.03 | 14 pg/ml |
| vWF | 10-0.5 mU/ml | 1/250 | 10.66 | 0.05 | 0.67 mU/ml |
| CD97 | 8000-125 pg/ml | 1/100 | 12.73 | 0.03 | 100 pg/ml |

CV: coefficient of variation; LLOD: lower limit of detection.

D. Statistical Analysis

The statistical methods used for the IPAS were previously described in Faca V. et al., J Proteome Res. 2006: 5(8):2009-2018; Faca V. et al., J Proteome Res. 2007: 6(9):3558-3565; and Paczesny S. et al., Science Translational Medicine. 2010: 2(13):13ra12. Differences in characteristics between patient groups were assessed with Kruska-Wallis tests for continuous values and chi-squared tests of association for categorical values. Protein concentrations from individual samples in the discovery and validation sets were compared using two sample t-tests. Receiver operating characteristic (ROC) areas under the curves (AUCs) were estimated nonparametrically. A ROC curve is a plot of the false positive rate on the x axis and true positive rate on the y axis for every possible level of a marker. A perfect test would have a ROC curve that is a right angle demonstrating 100% of true positives and no false positives. In this case, the corresponding Area Under the Curve (AUC) will equal to 1. A random test will have an AUC of 0.5 meaning there is one false positive for every true positive. Differences in median pre-HCT, day 0, +7, and +14 biomarker levels between SOS− and SOS+ patients were assessed using a Wilcoxon rank-sum test. Additionally, the differences in biomarkers trajectories were examined over time using a modeling approach.

E. Prognostic Bayesian Modeling

The plasma concentrations of 3 proteomic biomarkers (L-Ficolin, HA, and VCAM1) on the day of HCT were used to evaluate their prognostic performance for future occurrence of SOS onset. The clinical characteristics also included in the analysis were age, gender, donor type (related or unrelated), donor match (matched or mismatched), transplantation period (before or in 2005 or after 2005), transplantation number (1 or >1), conditioning regimen (chemotherapy only or combined with irradiation), busulfan (16 mg/kg) use in the conditioning (yes or no), and cyclophosphamide use in the conditioning (yes or no). Plasma protein concentrations and clinical characteristics were used as attributes for the prognosis of SOS onset. The Naïve Bayes classifier was selected for SOS onset prognosis because of its simplicity and high classification performance. Ten-fold cross-validation was used to avoid over training, bias, and/or artifacts. This Naïve Bayes classifier was developed with Waikato Environment for Knowledge Analysis software v3.6.10.

Example 1

In this Example, proteomic analysis was conducted to compare plasma pooled from 20 patients with SOS to plasma pooled from 20 patients without SOS. The clinical characteristics of patients are provided in Table 2.

TABLE 2

Clinical characteristics of patients in the discovery set

| Characteristic | | Discovery Cohort | | | Training Cohort | | | Independent Verification Cohort | | |
|---|---|---|---|---|---|---|---|---|---|---|
| | | SOS− (N = 20) | SOS+ (N = 20) | P | SOS− (N = 13) | SOS+ (N = 32) | P | SOS− (N = 22) | SOS+ (N = 13) | P |
| Age, years | Median | 43 | 43 | ns | 45 | 16 | 0.02 | 29 | 8 | 0.06 |
| | Range | 3-56 | 1-58 | | 3-55 | 1-58 | | 1-66 | 1-48 | |
| Disease, n (%) | Malignant* | 19 (95) | 17 (90) | ns | 12 (92) | 27 (84) | ns | 22 (100) | 13 (100) | ns |
| | Non-malignant† | 1 (5) | 2 (10) | | 1 (8) | 5 (16) | | 0 (0) | 0 (0) | |
| Donor type, n (%) | Related | 18 (90) | 17 (85) | ns | 12 (92) | 17 (53) | 0.02 | 14 (64) | 3 (33) | 0.02 |
| | Unrelated | 2 (10) | 3 (15) | | 1 (8) | 5 (16) | | 8 (36) | 10 (77) | |
| Donor match, n (%) | Matched | 20 (100) | 20 (100) | ns | 13 (100) | 25 (78) | 0.08 | 18 (82) | 47 (54) | ns |
| | Mismatched | 0 (0) | 0 (0) | | 0 (0) | 7 (22) | | 4 (18) | 6 (46) | |
| Conditioning regimen intensity, n (%)‡ | Full | 20 (100) | 20 (100) | ns | 13 (100) | 32 (100) | ns | 16 (73) | 13 (100) | ns |
| | With Busulfan (16 mg/kg, 4 days) | 14 (74) | 17 (90) | | 9 (69) | 26 (81) | | 1 (5) | 3 (23) | |
| | With TBI | 2 (10) | 1 (5) | | 2 (15) | 4 (12) | | 8 (36) | 6 (46) | |

TABLE 2-continued

Clinical characteristics of patients in the discovery set

| Characteristic | | Discovery Cohort | | | Training Cohort | | | Independent Verification Cohort | | |
|---|---|---|---|---|---|---|---|---|---|---|
| | | SOS− (N = 20) | SOS+ (N = 20) | P | SOS− (N = 13) | SOS+ (N = 32) | P | SOS− (N = 22) | SOS+ (N = 13) | P |
| GVHD prophylaxis regimen, n (%) | Tacro or CsA/MTX | 19 (95) | 18 (90) | ns | 12 (92) | 23 (72) | ns | 5 (23) | 5 (38) | ns |
| | With rapamycin | 0 (0) | 0 (0) | | 0 (0) | 1 (3) | | 6 (27) | 1 (8) | |
| | With MMF | 0 (0) | 0 (0) | | 0 (0) | 7 (22) | | 4 (18) | 4 (31) | |
| | Other§ | 1 (5) | 2 (10) | | 1 (8) | 1 (3) | | 1 (5) | 0 (0) | |
| | NA | 0 (0) | 0 (0) | | 0 (0) | 0 (0) | | 6 (27) | 3 (23) | |
| Time after HCT to SOS onset, day | Median | na | 14 | na | na | 11 | na | na | 9 | na |
| | Range | na | 4-37 | | na | 4-63 | | na | 5-23 | |
| Time after HCT to SOS sample acquisition, day | Median | 14 | 14 | ns | 14 | 11 | ns | 14 | 11 | ns |
| | Range | 7-41 | 7-37 | | 7-41 | 4-63 | | 7-14 | 5-23 | |
| Future acute GVHD 2-4, n (%) | Yes | 0 (0) | 0 (0) | ns | 0 (0) | 14 (44) | 0.004 | 0 (0) | 6 (46) | 0.0005 |
| | No | 20 (100) | 20 (100) | | 13 (100) | 18 (56) | | 22 (100) | 7 (54) | |
| Time after HCT to GVHD onset, day | Median | na | na | na | na | 33 | na | na | 21 | na |
| | Range | | | | | 14-75 | | | (11-46) | | na: not applicable,
ns: not significant;
TBI: total body irradiation;
Tacro: tacrolimus;
CsA: cyclosporine A;
MTX: methotrexate;
MMF: mycophenolate mofetil
*Malignant disease includes acute leukemia/myelodysplastic syndrome (n = 69), lymphoma (n = 18), multiple myeloma (n = 2), chronic leukemia (n = 13), myelofibrosis (n = 2), and paroxysmal nocturnal hemoglobinuria (PNH) (n = 2), neuroblastoma (n = 3), rhabdoid tumor (n = 1), and carcinoid tumor (n = 1).
†Non-malignant disease includes severe aplastic anemia (n = 2), thalassemia (n = 3), sickle cell disease (n = 2), chronic granulomatous disease (n = 1), and familial lymphohistiocytosis (n = 1).
‡Full-intensity conditioning regimens include: cyclophosphamide/etoposide/carmustine (CVB) (n = 7), busulfan (Bu)/cyclophosphamide (Cy) (n = 35), BAC (Bu [16 mg/kg], cytarabine [8000 mg/m²], and Cy [120 mg/kg] (n = 31), CyTBI (n = 21), fludarabine (Flu) or Clo + Bu (16 mg/kg) (n = 6), Busufan/Melphalan (n = 1), Flu/melphalan (n = 1), carboplatin/etoposide/melphalan (n = 4), carboplatin/thiotepa (n = 2), CyFlu (n = 4), and CyThiotepa (n = 2).
§Other GVHD prophylaxis included Tacro/corticosteroids (n = 3), MTX/corticosteroids (n = 2), Tacro/MTX/corticosteroids (n = 1).

Of 494 proteins identified and quantified, 151 proteins showed at least a 2-fold increase in the heavy/light isotope ratio, and 77 proteins showed a heavy-light isotope ratio of 0.5 or less (see Table 3 for complete summary) From the identified proteins, six proteins were selected for further analysis: L-Ficolin, VCAM1, TIMP1, vWF, and CD97. These proteins were selected based on the observation of at least a 2-fold increase or decrease in the heavy/light isotope ratio and their involvement in networks possibly involved in the pathogenesis of SOS. In addition, five endothelial markers (ST2, ANG2, HA, thrombomodulin, and PAI-1) were analyzed based on their involvement in SOS.

TABLE 3

Complete list of genes identified by MS-based proteomics in pooled plasma from SOS patients

| International Protein Index | Gene name | Gene Description | Ratio (mean) |
|---|---|---|---|
| IPI00295857 | COPA | coatomer subunit alpha. | 87.5 |
| IPI00028318 | PHACTR1 | isoform 1 of phosphatase and actin regulator 1. | 74.9 |
| IPI00004922 | CMA1 | chymase. | 67.3 |
| IPI00410333 | TREML1 | isoform 1 of trem-like transcript 1 protein precursor. | 33.1 |
| IPI00290035 | PCDH15 | protocadherin 15. | 23.7 |
| IPI00107155 | TMEM103 | isoform 1 of upf0405 protein tmem103. | 21.8 |
| IPI00410143 | CENPM | isoform 2 of centromere protein m. | 18.8 |
| IPI00787049 | DDT | similar to d-dopachrome decarboxylase. | 15.7 |
| IPI00012007 | AHCY | adenosylhomocysteinase. | 14.3 |
| IPI00218407 | ALDOB | fructose-bisphosphate aldolase b. | 13.9 |
| IPI00654755 | HBB | hemoglobin subunit beta. | 12.9 |
| IPI00010290 | FABP1 | fabp1 protein (fragment). | 11.8 |
| IPI00307781 | CHRDL2 | isoform 2 of chordin-like protein 2 precursor. | 10.5 |
| IPI00793758 | DCTN2 | 9 kda protein. | 10.1 |
| IPI00759493 | SUCLG1 | succinate-coa ligase, gdp-forming, alpha subunit. | 9.9 |
| IPI00400903 | C2orf46 | putative uncharacterized protein c2orf46. | 9.7 |
| IPI00306322 | COL4A2 | collagen alpha-2(iv) chain precursor. | 9.7 |
| IPI00792459 | HSPA8 | 23 kda protein. | 9.3 |
| IPI00016832 | PSMA1 | isoform short of proteasome subunit alpha type 1. | 9.0 |
| IPI00152591 | PGR | delta 4 progesterone receptor. | 8.9 |
| IPI00012828 | ACAA1 | 3-ketoacyl-coa thiolase, peroxisomal precursor. | 8.1 |
| IPI00219446 | PEBP1 | phosphatidylethanolamine-binding protein 1. | 8.0 |
| IPI00218733 | SOD1 | 16 kda protein. | 7.0 |
| IPI00301288 | SVEP1 | polydom. | 6.9 |

TABLE 3-continued

Complete list of genes identified by MS-based proteomics in pooled plasma from SOS patients

| International Protein Index | Gene name | Gene Description | Ratio (mean) |
|---|---|---|---|
| IPI00216085 | COX6B1 | cytochrome c oxidase subunit vib isoform 1. | 6.6 |
| IPI00465436 | CAT | catalase. | 6.6 |
| IPI00031008 | TNC | isoform 1 of tenascin precursor. | 6.5 |
| IPI00024993 | ECHS1 | enoyl-coa hydratase, mitochondrial precursor. | 6.2 |
| IPI00020977 | CTGF | isoform 1 of connective tissue growth factor precursor. | 6.2 |
| IPI00029039 | REG3A | regenerating islet-derived protein 3 alpha precursor. | 6.1 |
| IPI00025698 | LIMK2 | lim domain kinase 2 isoform 1. | 6.1 |
| IPI00291006 | MDH2 | malate dehydrogenase, mitochondrial precursor. | 6.1 |
| IPI00219038 | H3F3B | histone h3.3. | 5.7 |
| IPI00009440 | CYP8B1 | cytochrome p450 8b1. | 5.6 |
| IPI00029723 | FSTL1 | follistatin-related protein 1 precursor. | 5.5 |
| IPI00304962 | COL1A2 | collagen alpha-2(i) chain precursor. | 5.4 |
| IPI00299547 | LCN2 | neutrophil gelatinase-associated lipocalin precursor. | 5.3 |
| IPI00171516 | PLVAP | plasmalemma vesicle-associated protein. | 5.2 |
| IPI00031086 | IGFBP1 | insulin-like growth factor-binding protein 1 precursor. | 5.2 |
| IPI00032292 | TIMP1 | metalloproteinase inhibitor 1 precursor. | 4.8 |
| IPI00011522 | ACAA1 | *homo sapiens* clone 23623. | 4.7 |
| IPI00306543 | GDF15 | growth/differentiation factor 15 precursor. | 4.7 |
| IPI00005038 | HRSP12 | ribonuclease uk114. | 4.4 |
| IPI00022417 | LRG1 | leucine-rich alpha-2-glycoprotein precursor. | 4.4 |
| IPI00216138 | TAGLN | transgelin. | 4.4 |
| IPI00219025 | GLRX | glutaredoxin-1. | 4.4 |
| IPI00028911 | DAG1 | dystroglycan precursor. | 4.3 |
| IPI00549467 | NIT2 | nitrilase family member 2. | 4.3 |
| IPI00418471 | VIM | vimentin. | 4.2 |
| IPI00020687 | SPINK1 | pancreatic secretory trypsin inhibitor precursor. | 4.1 |
| IPI00745729 | SELENBP1 | 53 kda protein. | 4.1 |
| IPI00027038 | VSIG4 | isoform 1 of v-set and immunoglobulin domain-containing protein 4precursor. | 4.1 |
| IPI00026154 | PRKCSH | glucosidase 2 subunit beta precursor. | 4.0 |
| IPI00412546 | CR1 | complement receptor type 1 precursor. | 4.0 |
| IPI00000874 | PRDX1 | peroxiredoxin-1. | 3.9 |
| IPI00009027 | REG1A | lithostathine 1 alpha precursor. | 3.9 |
| IPI00015881 | CSF1 | isoform 1 of macrophage colony-stimulating factor 1 precursor. | 3.8 |
| IPI00647950 | DLG2 | isoform 2 of discs large homolog 2. | 3.8 |
| IPI00549411 | OR51E1/PSGR2 | dresden-g-protein-coupled receptor. | 3.8 |
| IPI00019038 | LYZ | lysozyme c precursor. | 3.7 |
| IPI00215746 | FABP4 | fatty acid-binding protein, adipocyte. | 3.6 |
| IPI00383032 | HAVCR2 | isoform 2 of hepatitis a virus cellular receptor 2 precursor. | 3.6 |
| IPI00305975 | SPON2 | spondin-2 precursor. | 3.6 |
| IPI00297646 | COL1A1 | collagen alpha-1(i) chain precursor. | 3.4 |
| IPI00020356 | MAP1A | 331 kda protein. | 3.3 |
| IPI00465248 | ENO1 | isoform alpha-enolase of alpha-enolase. | 3.3 |
| IPI00293276 | MIF | macrophage migration inhibitory factor. | 3.3 |
| IPI00022892 | THY1 | thy-1 membrane glycoprotein precursor. | 3.3 |
| IPI00298388 | PIK3IP1 | isoform 1 of phosphoinositide-3-kinase-interacting protein 1precursor. | 3.3 |
| IPI00003933 | HAGH | hydroxyacyl glutathione hydrolase isoform 1. | 3.2 |
| IPI00002324 | MAT2B | isoform 1 of methionine adenosyltransferase 2 subunit beta. | 3.2 |
| IPI00011229 | CTSD | cathepsin d precursor. | 3.1 |
| IPI00001528 | IL18BP | isoform c of interleukin-18-binding protein precursor. | 3.1 |
| IPI00295741 | CTSB | cathepsin b precursor. | 3.1 |
| IPI00298547 | PARK7 | protein dj-1. | 3.0 |
| IPI00039050 | FOLR2 | folate binding protein. | 3.0 |
| IPI00216318 | YWHAB | isoform long of 14-3-3 protein beta/alpha. | 3.0 |
| IPI00022200 | COL6A3 | alpha 3 type vi collagen isoform 1 precursor. | 3.0 |
| IPI00465028 | TPI1 | triosephosphate isomerase 1 variant. | 3.0 |
| IPI00419990 | PTCRA | pre-t-cell antigen receptor alpha. | 2.9 |
| IPI00219910 | BLVRB | 23 kda protein. | 2.9 |
| IPI00514310 | F11R | isoform 4 of putative thiosulfate sulfurtransferase kat. | 2.9 |
| IPI00004656 | B2M | beta-2-microglobulin precursor. | 2.9 |
| IPI00008298 | DEFA5 | defensin 5 precursor. | 2.9 |
| IPI00299412 | CD97 | isoform 2 of cd97 antigen precursor. | 2.9 |
| IPI00000144 | OXT | oxytocin-neurophysin 1 precursor. | 2.9 |

TABLE 3-continued

Complete list of genes identified by MS-based proteomics in pooled plasma from SOS patients

| International Protein Index | Gene name | Gene Description | Ratio (mean) |
|---|---|---|---|
| IPI00000335 | HINT2 | histidine triad nucleotide-binding protein 2. | 2.8 |
| IPI00008494 | ICAM1 | intercellular adhesion molecule 1 precursor. | 2.7 |
| IPI00002535 | FKBP2 | fk506-binding protein 2 precursor. | 2.7 |
| IPI00029658 | EFEMP1 | isoform 1 of egf-containing fibulin-like extracellular matrix protein 1 precursor. | 2.7 |
| IPI00011302 | CD59 | cd59 glycoprotein precursor. | 2.7 |
| IPI00219018 | GAPDH | glyceraldehyde-3-phosphate dehydrogenase. | 2.7 |
| IPI00018136 | VCAM1 | isoform 1 of vascular cell adhesion protein 1 precursor. | 2.7 |
| IPI00414784 | CD300A | isoform 1 of cmrf35-h antigen precursor. | 2.6 |
| IPI00104074 | CD163 | isoform 1 of scavenger receptor cysteine-rich type 1 protein m130 precursor. | 2.6 |
| IPI00032876 | CYTL1 | cytokine-like protein 1 precursor. | 2.6 |
| IPI00289275 | CILP | cartilage intermediate layer protein 1 precursor. | 2.6 |
| IPI00013895 | S100A11 | protein s100-a11. | 2.6 |
| IPI00304483 | PAIP2 | polyadenylate-binding protein-interacting protein 2. | 2.5 |
| IPI00291170 | KIAA1199 | isoform 2 of protein kiaa 1199 precursor. | 2.5 |
| IPI00023648 | ISLR | immunoglobulin superfamily containing leucine-rich repeat. | 2.5 |
| IPI00022284 | PRNP | major prion protein precursor. | 2.5 |
| IPI00014048 | RNASE1 | ribonuclease pancreatic precursor. | 2.5 |
| IPI00216298 | TXN | thioredoxin. | 2.5 |
| IPI00472035 | MICA | isoform 2 of hla class i histocompatibility antigen, cw-16 alpha chain precursor. | 2.5 |
| IPI00334254 | EGFLAM | egf-like, fibronectin type iii and laminin g domains isoform 2. | 2.5 |
| IPI00642816 | SRP9 | signal recognition particle 9 kda protein. | 2.5 |
| IPI00291488 | WFDC2 | isoform 1 of wap four-disulfide core domain protein 2 precursor. | 2.5 |
| IPI00375441 | FUBP1 | isoform 1 of far upstream element-binding protein 1. | 2.4 |
| IPI00016915 | IGFBP7 | insulin-like growth factor-binding protein 7 precursor. | 2.4 |
| IPI00103871 | ROBO4 | isoform 1 of roundabout homolog 4 precursor. | 2.4 |
| IPI00784257 | FOLR2 | folate receptor beta precursor. | 2.4 |
| IPI00301579 | NPC2 | epididymal secretory protein e1 precursor. | 2.4 |
| IPI00003440 | CCL15 | small inducible cytokine a15 precursor. | 2.4 |
| IPI00328550 | THBS4 | thrombospondin-4 precursor. | 2.4 |
| IPI00014953 | NHLRC2 | cdna flj20147 fis, clone col07954. | 2.4 |
| IPI00023014 | VWF | von willebrand factor precursor. | 2.3 |
| IPI00062700 | TIMD4 | t-cell immunoglobulin and mucin domain-containing protein 4 precursor. | 2.3 |
| IPI00029863 | SERPINF2 | alpha-2-antiplasmin precursor. | 2.3 |
| IPI00294615 | FBLN5 | fibulin-5 precursor. | 2.3 |
| IPI00465439 | ALDOA | fructose-bisphosphate aldolase a. | 2.3 |
| IPI00025846 | DSC2 | isoform 2a of desmocollin-2 precursor. | 2.2 |
| IPI00022426 | AMBP | ambp protein precursor. | 2.2 |
| IPI00791848 | SIPA1L3 | similar to signal-induced proliferation-associated 1 like protein 3. | 2.2 |
| IPI00003375 | CCL14 | isoform hcc-1 of small inducible cytokine a14 precursor. | 2.2 |
| IPI00014263 | EIF4H | isoform long of eukaryotic translation initiation factor 4h. | 2.2 |
| IPI00167498 | C9orf93 | isoform 2 of uncharacterized protein c9orf93. | 2.2 |
| IPI00021439 | ACTB | actin, cytoplasmic 1. | 2.2 |
| IPI00215760 | FMO5 | dimethylaniline monooxygenase [n-oxide-forming] 5. | 2.2 |
| IPI00019449 | RNASE2 | nonsecretory ribonuclease precursor. | 2.1 |
| IPI00022974 | PIP | prolactin-inducible protein precursor. | 2.1 |
| IPI00101678 | KAZALD1 | isoform 1 of kazal-type serine protease inhibitor domain-containing protein 1 precursor. | 2.1 |
| IPI00297284 | IGFBP2 | insulin-like growth factor-binding protein 2 precursor. | 2.1 |
| IPI00179851 | C11orf9 | imp dehydrogenase/gmp reductase family protein. | 2.1 |
| IPI00296777 | SPARCL1 | sparc-like protein 1 precursor. | 2.1 |
| IPI00009521 | MARCO | macrophage receptor marco. | 2.1 |
| IPI00293487 | REC8 | meiotic recombination protein rec8-like 1. | 2.1 |
| IPI00009822 | SRP54 | signal recognition particle 54 kda protein. | 2.1 |
| IPI00011385 | LOXL3 | lysyl oxidase homolog 3 precursor. | 2.1 |
| IPI00025426 | PZP | pregnancy zone protein precursor. | 2.1 |
| IPI00027827 | SOD3 | extracellular superoxide dismutase [cu—zn] precursor. | 2.1 |

TABLE 3-continued

Complete list of genes identified by MS-based
proteomics in pooled plasma from SOS patients

| International Protein Index | Gene name | Gene Description | Ratio (mean) |
|---|---|---|---|
| IPI00031490 | COLEC11 | collectin sub-family member 11 isoform a. | 2.1 |
| IPI00299485 | CD93 | complement component c1q receptor precursor. | 2.1 |
| IPI00290856 | XLKD1 | lymphatic vessel endothelial hyaluronic acid receptor 1 precursor. | 2.1 |
| IPI00020990 | OMD | osteomodulin precursor. | 2.0 |
| IPI00024915 | PRDX5 | isoform mitochondrial of peroxiredoxin-5, mitochondrial precursor. | 2.0 |
| IPI00019579 | CFD | complement factor d precursor. | 2.0 |
| IPI00386854 | HNRPA2B1 | hnrpa2b1 protein. | 2.0 |
| IPI00008780 | STC2 | stanniocalcin-2 precursor. | 2.0 |
| IPI00025204 | CD5L | cd5 antigen-like precursor. | 2.0 |
| IPI00299181 | OR2F1 | olfactory receptor 2f1. | 2.0 |
| IPI00007797 | FABP5 | fatty acid-binding protein, epidermal. | 1.9 |
| IPI00004480 | ADAMDEC1 | adam dec1 precursor. | 1.9 |
| IPI00215767 | B4GALT1 | isoform long of beta-1,4-galactosyltransferase 1. | 1.9 |
| IPI00018880 | TNFRSF1A | tumor necrosis factor receptor superfamily member 1a precursor. | 1.9 |
| IPI00006608 | APP | isoform app770 of amyloid beta a4 protein precursor (fragment). | 1.9 |
| IPI00024284 | HSPG2 | basement membrane-specific heparan sulfate proteoglycan core proteinprecursor. | 1.9 |
| IPI00328703 | OAF | oaf homolog. | 1.9 |
| IPI00032293 | CST3 | cystatin-c precursor. | 1.9 |
| IPI00029260 | CD14 | monocyte differentiation antigen cd14 precursor. | 1.9 |
| IPI00011155 | ASGR2 | isoform 1 of asialoglycoprotein receptor 2. | 1.9 |
| IPI00218803 | FBLN1 | isoform b of fibulin-1 precursor. | 1.8 |
| IPI00419966 | ABI3BP | isoform 2 of target of nesh-sh3 precursor. | 1.8 |
| IPI00029235 | IGFBP6 | insulin-like growth factor-binding protein 6 precursor. | 1.8 |
| IPI00292150 | LTBP2 | latent-transforming growth factor beta-binding protein 2 precursor. | 1.8 |
| IPI00550991 | SERPINA3 | isoform 1 of alpha-1-antichymotrypsin precursor. | 1.8 |
| IPI00023505 | FCGR2A | low affinity immunoglobulin gamma fc region receptor ii-a precursor. | 1.8 |
| IPI00022810 | CTSC | dipeptidyl-peptidase 1 precursor. | 1.8 |
| IPI00009802 | VCAN | isoform v0 of versican core protein precursor. | 1.8 |
| IPI00305380 | IGFBP4 | insulin-like growth factor-binding protein 4 precursor. | 1.8 |
| IPI00015525 | MMRN2 | multimerin-2 precursor. | 1.8 |
| IPI00021891 | FGG | isoform gamma-b of fibrinogen gamma chain precursor. | 1.8 |
| IPI00007067 | C9orf19 | golgi-associated plant pathogenesis-related protein 1. | 1.8 |
| IPI00219219 | LGALS1 | galectin-1. | 1.7 |
| IPI00028413 | ITIH3 | inter-alpha-trypsin inhibitor heavy chain h3 precursor. | 1.7 |
| IPI00023673 | LGALS3BP | galectin-3-binding protein precursor. | 1.7 |
| IPI00003648 | PVRL1 | isoform delta of poliovirus receptor-related protein 1 precursor. | 1.7 |
| IPI00303161 | ESAM | endothelial cell-selective adhesion molecule precursor. | 1.7 |
| IPI00332887 | SIRPA | signal-regulatory protein alpha precursor. | 1.7 |
| IPI00021923 | FAM3C | protein fam3c precursor. | 1.7 |
| IPI00011876 | MTAP | s-methyl-5-thioadenosine phosphorylase. | 1.7 |
| IPI00019954 | CST6 | cystatin-m precursor. | 1.7 |
| IPI00022620 | SLURP1 | secreted ly-6/upar-related protein 1 precursor. | 1.7 |
| IPI00418262 | ALDOC | fructose-bisphosphate aldolase c. | 1.7 |
| IPI00008580 | SLPI | Antileuko proteinase precursor. | 1.7 |
| IPI00298497 | FGB | fibrinogen beta chain precursor. | 1.7 |
| IPI00294705 | PAPLN | papilin. | 1.7 |
| IPI00296083 | SFTPB | pulmonary surfactant-associated protein b precursor. | 1.6 |
| IPI00179164 | KIAA1244 | sec7-like domain containing protein. | 1.6 |
| IPI00294193 | TMEM110 | isoform 1 of inter-alpha-trypsin inhibitor heavy chain h4 precursor. | 1.6 |
| IPI00027983 | CDA | cytidine deaminase. | 1.6 |
| IPI00299435 | APOF | apolipoprotein f precursor. | 1.6 |
| IPI00022933 | CD74 | isoform long of hla class ii histocompatibility antigen gamma chain. | 1.6 |

TABLE 3-continued

Complete list of genes identified by MS-based proteomics in pooled plasma from SOS patients

| International Protein Index | Gene name | Gene Description | Ratio (mean) |
|---|---|---|---|
| IPI00328746 | RTN4RL2 | reticulon-4 receptor-like 2 precursor. | 1.6 |
| IPI00026199 | GPX3 | glutathione peroxidase 3 precursor. | 1.6 |
| IPI00376353 | ANKRD37 | ankyrin repeat domain-containing protein 37. | 1.6 |
| IPI00013303 | LSAMP | limbic system-associated membrane protein precursor. | 1.6 |
| IPI00297160 | CD44 | isoform 12 of cd44 antigen precursor. | 1.6 |
| IPI00007425 | DSC1 | desmocollin 1 isoform dsc1b preproprotein. | 1.6 |
| IPI00297444 | CD177 | isoform 1 of cd177 antigen precursor. | 1.6 |
| IPI00419585 | PPIA | peptidyl-prolyl cis-trans isomerase a. | 1.5 |
| IPI00029699 | RNASE4 | ribonuclease 4 precursor. | 1.5 |
| IPI00013894 | STIP1 | stress-induced-phosphoprotein 1. | 1.5 |
| IPI00217481 | GPR126 | developmentally regulated g-protein-coupled receptor beta 1. | 1.5 |
| IPI00010295 | CPN1 | carboxypeptidase n catalytic chain precursor. | 1.5 |
| IPI00030871 | VNN1 | pantetheinase precursor. | 1.5 |
| IPI00303966 | C6orf155 | uncharacterized protein c6orf155. | 1.5 |
| IPI00021834 | TFPI | isoform alpha of tissue factor pathway inhibitor precursor. | 1.5 |
| IPI00478816 | SPINK5 | serine protease inhibitor kazal-type 5 precursor. | 1.5 |
| IPI00148061 | LDHAL6A | l-lactate dehydrogenase a-like 6a. | 1.5 |
| IPI00005142 | FGFR1 | isoform 1 of basic fibroblast growth factor receptor 1 precursor. | 1.5 |
| IPI00022429 | ORM1 | alpha-1-acid glycoprotein 1 precursor. | 1.5 |
| IPI00006988 | RETN | resistin precursor. | 1.5 |
| IPI00030075 | FGL2 | fibroleukin precursor. | 1.5 |
| IPI00021885 | FGA | isoform 1 of fibrinogen alpha chain precursor. | 1.5 |
| IPI00015102 | ALCAM | isoform 1 of cd166 antigen precursor. | 1.5 |
| IPI00028030 | COMP | cartilage oligomeric matrix protein precursor. | 1.4 |
| IPI00016112 | PXDN | peroxidasin homolog. | 1.4 |
| IPI00334238 | NPTXR | neuronal pentraxin receptor. | 1.4 |
| IPI00297412 | CADPS | isoform 1 of calcium-dependent secretion activator 1. | 1.4 |
| IPI00220857 | CAST | isoform 2 of calpastatin. | 1.4 |
| IPI00045600 | DAB2IP | dab2 interacting protein isoform 1. | 1.4 |
| IPI00470535 | CACNA2D1 | dihydropyridine receptor alpha 2 subunit. | 1.4 |
| IPI00395488 | VASN | vasorin precursor. | 1.4 |
| IPI00017601 | CP | ceruloplasmin precursor. | 1.4 |
| IPI00176221 | NEGR1 | neuronal growth regulator 1 precursor. | 1.4 |
| IPI00374316 | C6orf115 | similar to protein c6orf115. | 1.4 |
| IPI00026183 | CCL18 | small inducible cytokine a18 precursor. | 1.4 |
| IPI00290283 | MASP1 | mannan-binding lectin serine protease 1 isoform 2 precursor. | 1.4 |
| IPI00027972 | LILRA2 | isoform 1 of leukocyte immunoglobulin-like receptor subfamily a member 2 precursor. | 1.4 |
| IPI00299738 | PCOLCE | procollagen c-endopeptidase enhancer 1 precursor. | 1.4 |
| IPI00303963 | C2 | complement c2 precursor (fragment). | 1.4 |
| IPI00374068 | ADAMTSL4 | isoform 1 of adamts-like protein 4 precursor. | 1.4 |
| IPI00291866 | SERPING1 | plasma protease c1 inhibitor precursor. | 1.4 |
| IPI00027507 | CFHR3 | complement factor h-related protein 3 precursor. | 1.4 |
| IPI00791350 | CLEC3B | 11 kda protein. | 1.4 |
| IPI00301143 | PI16 | isoform 1 of peptidase inhibitor 16 precursor. | 1.4 |
| IPI00020986 | LUM | lumican precursor. | 1.4 |
| IPI00021842 | APOE | apolipoprotein e precursor. | 1.4 |
| IPI00021578 | CFHR4 | complement factor h-related protein 4 precursor. | 1.3 |
| IPI00022418 | FN1 | isoform 1 of fibronectin precursor. | 1.3 |
| IPI00027166 | TIMP2 | metalloproteinase inhibitor 2 precursor. | 1.3 |
| IPI00644346 | ADAMTSL2 | adamts-like protein 2 precursor. | 1.3 |
| IPI00032258 | C4A | complement c4-a precursor. | 1.3 |
| IPI00011651 | PTPRG | isoform 1 of receptor-type tyrosine-protein phosphatase gammaprecursor. | 1.3 |
| IPI00396077 | TOPORS | isoform 1 of e3 ubiquitin-protein ligase topors. | 1.3 |
| IPI00008433 | RPS5 | 40s ribosomal protein s5. | 1.3 |
| IPI00029168 | LPA | apolipoprotein. | 1.3 |
| IPI00216882 | MASP1 | mannan-binding lectin serine protease 1 isoform 3. | 1.3 |
| IPI00299150 | CTSS | cathepsin s precursor. | 1.3 |
| IPI00003351 | ECM1 | extracellular matrix protein 1 precursor. | 1.3 |
| IPI00465322 | BOC | 121 kda protein. | 1.3 |
| IPI00218795 | SELL | l-selectin precursor. | 1.3 |
| IPI00293565 | FLT4 | fms-related tyrosine kinase 4 isoform 1. | 1.3 |
| IPI00397717 | SYCN | syncollin. | 1.3 |
| IPI00299307 | MASP1 | complement-activating component of ra-reactive factor precursor. | 1.3 |

TABLE 3-continued

Complete list of genes identified by MS-based proteomics in pooled plasma from SOS patients

| International Protein Index | Gene name | Gene Description | Ratio (mean) |
|---|---|---|---|
| IPI00020091 | ORM2 | alpha-1-acid glycoprotein 2 precursor. | 1.3 |
| IPI00294713 | MASP2 | isoform 1 of mannan-binding lectin serine protease 2 precursor. | 1.3 |
| IPI00291316 | ARHGEF2 | rho/rac guanine nucleotide exchange factor (gef) 2. | 1.3 |
| IPI00478414 | CHRDL1 | ventroptin (fragment). | 1.2 |
| IPI00022395 | C9 | complement component c9 precursor. | 1.2 |
| IPI00004084 | CREBL1 | isoform 2 of cyclic amp-dependent transcription factor atf-6 beta. | 1.2 |
| IPI00329104 | LILRA3 | leukocyte immunoglobulin-like receptor subfamily a member 3 precursor. | 1.2 |
| IPI00296165 | C1R | complement c1r subcomponent precursor. | 1.2 |
| IPI00015029 | PTGES3 | prostaglandin e synthase 3. | 1.2 |
| IPI00296608 | C7 | complement component c7 precursor. | 1.2 |
| IPI00006717 | CCL16 | small inducible cytokine a16 precursor. | 1.2 |
| IPI00478003 | A2M | alpha-2-macroglobulin precursor. | 1.2 |
| IPI00006662 | APOD | apolipoprotein d precursor. | 1.2 |
| IPI00025285 | ATP6V1G1 | vacuolar atp synthase subunit g 1. | 1.2 |
| IPI00009793 | C1RL | complement c1r-like protein. | 1.2 |
| IPI00219861 | ACP1 | isoform 1 of low molecular weight phosphotyrosine protein phosphatase. | 1.2 |
| IPI00796830 | A2M | 13 kda protein. | 1.2 |
| IPI00604691 | GPR157 | hypothetical protein (fragment). | 1.2 |
| IPI00025864 | BCHE | cholinesterase precursor. | 1.2 |
| IPI00003817 | ARHGDIB | rho gdp-dissociation inhibitor 2. | 1.2 |
| IPI00006114 | SERPINF1 | pigment epithelium-derived factor precursor. | 1.2 |
| IPI00004373 | MBL2 | mannose-binding protein c precursor. | 1.2 |
| IPI00742705 | MAP3K14 | 6 kda protein. | 1.2 |
| IPI00477992 | C1QB | complement component 1, q subcomponent, b chain precursor. | 1.2 |
| IPI00011036 | INHBE | inhibin beta e chain precursor. | 1.2 |
| IPI00019591 | CFB | isoform 1 of complement factor b precursor (fragment). | 1.2 |
| IPI00007047 | S100A8 | protein s100-a8. | 1.2 |
| IPI00022895 | A1BG | alpha-1b-glycoprotein precursor. | 1.2 |
| IPI00555812 | GC | vitamin d-binding protein precursor. | 1.2 |
| IPI00000075 | TGFB1 | transforming growth factor beta-1 precursor. | 1.1 |
| IPI00027780 | MMP2 | 72 kda type iv collagenase precursor. | 1.1 |
| IPI00414283 | FN1 | fibronectin 1 isoform 4 preproprotein. | 1.1 |
| IPI00000879 | TXK | tyrosine-protein kinase txk. | 1.1 |
| IPI00298003 | SEMA3F | semaphorin-3f precursor. | 1.1 |
| IPI00387168 | PCSK9 | isoform 1 of proprotein convertase subtilisin/kexin type 9 precursor. | 1.1 |
| IPI00029739 | CFH | isoform 1 of complement factor h precursor. | 1.1 |
| IPI00011252 | C8A | complement component c8 alpha chain precursor. | 1.1 |
| IPI00292530 | ITIH1 | inter-alpha-trypsin inhibitor heavy chain h1 precursor. | 1.1 |
| IPI00299059 | CHL1 | isoform 2 of neural cell adhesion molecule l1-like protein precursor. | 1.1 |
| IPI00022394 | C1QC | complement c1q subcomponent subunit c precursor. | 1.1 |
| IPI00027774 | THAP2 | thap domain-containing protein 2. | 1.1 |
| IPI00006154 | CFHR2 | isoform long of complement factor h-related protein 2 precursor. | 1.1 |
| IPI00032328 | KNG1 | isoform hmw of kininogen-1 precursor. | 1.1 |
| IPI00738433 | CPN2 | similar to carboxypeptidase n subunit 2 precursor. | 1.1 |
| IPI00026314 | GSN | isoform 1 of gelsolin precursor. | 1.1 |
| IPI00022371 | HRG | histidine-rich glycoprotein precursor. | 1.1 |
| IPI00009028 | CLEC3B | tetranectin precursor. | 1.1 |
| IPI00022488 | HPX | hemopexin precursor. | 1.1 |
| IPI00294469 | COQ4 | ubiquinone biosynthesis protein coq4 homolog. | 1.1 |
| IPI00041065 | HABP2 | hyaluronan-binding protein 2 precursor. | 1.1 |
| IPI00017696 | C1S | complement c1s subcomponent precursor. | 1.0 |
| IPI00742696 | GC | vitamin d-binding protein precursor. | 1.0 |
| IPI00027396 | HN1L | isoform 1 of protein cramped-like. | 1.0 |
| IPI00220327 | KRT1 | keratin, type ii cytoskeletal 1. | 1.0 |
| IPI00007244 | MPO | isoform h17 of myeloperoxidase precursor. | 1.0 |
| IPI00218732 | PON1 | serum paraoxonase/arylesterase 1. | 1.0 |
| IPI00019576 | F10 | coagulation factor x precursor. | 1.0 |
| IPI00215894 | KNG1 | isoform lmw of kininogen-1 precursor. | 1.0 |
| IPI00291867 | CFI | complement factor i precursor. | 1.0 |
| IPI00218192 | ITIH4 | isoform 2 of inter-alpha-trypsin inhibitor heavy chain h4 precursor. | 1.0 |

TABLE 3-continued

Complete list of genes identified by MS-based
proteomics in pooled plasma from SOS patients

| International Protein Index | Gene name | Gene Description | Ratio (mean) |
|---|---|---|---|
| IPI00792115 | CLEC3B | hypothetical protein dkfzp686h17246. | 1.0 |
| IPI00375682 | NRK | isoform 1 of nik-related protein kinase. | 1.0 |
| IPI00479116 | CPN2 | carboxypeptidase n subunit 2 precursor. | 1.0 |
| IPI00760855 | TMEM110 | 101 kda protein. | 1.0 |
| IPI00019176 | RARRES2 | retinoic acid receptor responder protein 2 precursor. | 1.0 |
| IPI00064534 | CIZ1 | cdna flj14381 fis, clone hemba1001824, highly similar to homo sapiens nuclear protein np94 mrna. | 1.0 |
| IPI00021085 | PGLYRP1 | peptidoglycan recognition protein precursor. | 1.0 |
| IPI00303292 | KPNA1 | importin alpha-1 subunit. | 1.0 |
| IPI00654888 | KLKB1 | kallikrein b, plasma (fletcher factor) 1. | 1.0 |
| IPI00017841 | OLFM1 | isoform 1 of noelin precursor. | 1.0 |
| IPI00023314 | INHBC | inhibin beta c chain precursor. | 1.0 |
| IPI00298860 | LTF | growth-inhibiting protein 12. | 1.0 |
| IPI00305461 | ITIH2 | inter-alpha-trypsin inhibitor heavy chain h2 precursor. | 1.0 |
| IPI00004944 | SLC4A10 | isoform 1 of sodium-driven chloride bicarbonate exchanger. | 1.0 |
| IPI00296176 | F9 | coagulation factor ix precursor. | 1.0 |
| IPI00011264 | CFHR1 | complement factor h-related protein 1 precursor. | 1.0 |
| IPI00291262 | CLU | clusterin precursor. | 1.0 |
| IPI00218413 | BTD | biotinidase precursor. | 1.0 |
| IPI00007199 | SERPINA10 | protein z-dependent protease inhibitor precursor. | 1.0 |
| IPI00005721 | DEFA1 | neutrophil defensin 1 precursor. | 1.0 |
| IPI00009920 | C6 | complement component c6 precursor. | 1.0 |
| IPI00006543 | CFHR5 | complement factor h-related 5. | 1.0 |
| IPI00019568 | F2 | prothrombin precursor (fragment). | 1.0 |
| IPI00011261 | C8G | complement component c8 gamma chain precursor. | 1.0 |
| IPI00783987 | C3 | complement c3 precursor (fragment). | 1.0 |
| IPI00235003 | FAS | tumor necrosis factor receptor superfamily, member 6 isoform 1 variant | 1.0 |
| IPI00022431 | AHSG | alpha-2-hs-glycoprotein precursor. | 0.9 |
| IPI00032179 | SERPINC1 | antithrombin iii variant. | 0.9 |
| IPI00643525 | C4A | complement component 4a. | 0.9 |
| IPI00164623 | C3 | 187 kda protein. | 0.9 |
| IPI00171678 | DBH | dopamine beta-hydroxylase precursor. | 0.9 |
| IPI00795830 | AHSG | 29 kda protein. | 0.9 |
| IPI00010402 | SH3BGRL3 | hypothetical protein. | 0.9 |
| IPI00293925 | FCN3 | isoform 1 of ficolin-3 precursor. | 0.9 |
| IPI00479186 | PKM2 | isoform m2 of pyruvate kinase isozymes m1/m2. | 0.9 |
| IPI00027235 | ATRN | isoform 1 of attractin precursor. | 0.9 |
| IPI00029061 | SEPP1 | selenoprotein p precursor. | 0.9 |
| IPI00012503 | PSAP | isoform sap-mu-0 of proactivator polypeptide precursor. | 0.9 |
| IPI00298828 | APOH | beta-2-glycoprotein 1 precursor. | 0.9 |
| IPI00007240 | F13B | coagulation factor xiii b chain precursor. | 0.9 |
| IPI00031392 | CARD14 | caspase recruitment domain protein 14 isoform 2. | 0.9 |
| IPI00019530 | TIE1 | tyrosine-protein kinase receptor tie-1 precursor. | 0.9 |
| IPI00032291 | C5 | complement c5 precursor. | 0.9 |
| IPI00418163 | C4B | complement component 4b preproprotein. | 0.9 |
| IPI00004372 | MEP1A | meprin a subunit alpha precursor. | 0.9 |
| IPI00294395 | C8B | complement component c8 beta chain precursor. | 0.9 |
| IPI00029236 | IGFBP5 | insulin-like growth factor-binding protein 5 precursor. | 0.9 |
| IPI00022229 | APOB | apolipoprotein b-100 precursor. | 0.9 |
| IPI00030739 | APOM | apolipoprotein m. | 0.9 |
| IPI00242956 | FCGBP | iggfc-binding protein precursor. | 0.9 |
| IPI00008556 | F11 | isoform 1 of coagulation factor xi precursor. | 0.9 |
| IPI00645051 | BBS1 | bbs1 protein. | 0.8 |
| IPI00789477 | LTF | 73 kda protein. | 0.8 |
| IPI00022331 | LCAT | phosphatidylcholine-sterol acyltransferase precursor. | 0.8 |
| IPI00298971 | VTN | vitronectin precursor. | 0.8 |
| IPI00009938 | CEACAM1 | isoform a of carcinoembryonic antigen-related cell adhesion molecule 1 precursor. | 0.8 |
| IPI00744286 | B3GALNT2 | isoform 2 of udp-galnac: beta-1,3-n-acetylgalactosaminyltransferase 2. | 0.8 |
| IPI00022420 | RBP4 | plasma retinol-binding protein precursor. | 0.8 |
| IPI00021727 | C4BPA | c4b-binding protein alpha chain precursor. | 0.8 |
| IPI00019580 | PLG | plasminogen precursor. | 0.8 |

TABLE 3-continued

Complete list of genes identified by MS-based proteomics in pooled plasma from SOS patients

| International Protein Index | Gene name | Gene Description | Ratio (mean) |
|---|---|---|---|
| IPI00296840 | POLI | dna polymerase iota. | 0.8 |
| IPI00297655 | NOTCH2 | neurogenic locus notch homolog protein 2 precursor. | 0.8 |
| IPI00021364 | CFP | properdin precursor. | 0.8 |
| IPI00001754 | F11R | junctional adhesion molecule a precursor. | 0.8 |
| IPI00025862 | C4BPB | isoform 1 of c4b-binding protein beta chain precursor. | 0.8 |
| IPI00328113 | FBN1 | fibrillin-1 precursor. | 0.8 |
| IPI00292218 | MST1 | hepatocyte growth factor-like protein precursor. | 0.8 |
| IPI00163207 | PGLYRP2 | isoform 1 of n-acetylmuramoyl-l-alanine amidase precursor. | 0.8 |
| IPI00024825 | PRG4 | isoform a of proteoglycan-4 precursor. | 0.8 |
| IPI00023019 | SHBG | isoform 1 of sex hormone-binding globulin precursor. | 0.8 |
| IPI00220249 | LTBP1 | latent-transforming growth factor beta-binding protein, isoform 1lprecursor. | 0.8 |
| IPI00013418 | BIRC2 | baculoviral iap repeat-containing protein 2. | 0.7 |
| IPI00019943 | AFM | afamin precursor. | 0.7 |
| IPI00216691 | PFN1 | profilin-1. | 0.7 |
| IPI00011255 | GP1BA | platelet glycoprotein ib alpha chain precursor. | 0.7 |
| IPI00382606 | F7 | factor vii active site mutant immunoconjugate. | 0.7 |
| IPI00007634 | LIMS1 | lim and senescent cell antigen-like-containing domain protein 1. | 0.7 |
| IPI00004798 | CRISP3 | cysteine-rich secretory protein 3 precursor. | 0.7 |
| IPI00657788 | LAIR1 | 30 kda protein. | 0.7 |
| IPI00655676 | PRG4 | isoform d of proteoglycan-4 precursor. | 0.7 |
| IPI00220644 | PKM2 | isoform m1 of pyruvate kinase isozymes m1/m2. | 0.7 |
| IPI00001611 | IGF2 | isoform 1 of insulin-like growth factor ii precursor. | 0.7 |
| IPI00432707 | CASP12 | caspase-12. | 0.7 |
| IPI00021854 | APOA2 | apolipoprotein a-ii precursor. | 0.7 |
| IPI00294250 | EPHA1 | ephrin type-a receptor 1 precursor. | 0.7 |
| IPI00168459 | PHLDB2 | isoform 2 of pleckstrin homology-like domain family b member 2. | 0.7 |
| IPI00294004 | PROS1 | vitamin k-dependent protein s precursor. | 0.7 |
| IPI00021817 | PROC | vitamin k-dependent protein c precursor. | 0.7 |
| IPI00217405 | UBR1 | isoform 1 of e3 ubiquitin-protein ligase ubr1. | 0.7 |
| IPI00005439 | FETUB | fetuin-b precursor. | 0.6 |
| IPI00012011 | CFL1 | cofilin-1. | 0.6 |
| IPI00170692 | VAPA | vesicle-associated membrane protein-associated protein a. | 0.6 |
| IPI00018305 | IGFBP3 | insulin-like growth factor-binding protein 3 precursor. | 0.6 |
| IPI00002714 | DKK3 | dickkopf-related protein 3 precursor. | 0.6 |
| IPI00220257 | TTLL1 | isoform 3 of probable tubulin polyglutamylase. | 0.6 |
| IPI00296713 | GRN | isoform 1 of granulins precursor. | 0.6 |
| IPI00220901 | TBC1D4 | tbc1 domain family member 4. | 0.6 |
| IPI00027255 | MYL6B | myosin light polypeptide 6b. | 0.6 |
| IPI00168262 | GLT25D1 | cdna psec0241 fis, clone nt2rp3000234, moderately similar to *homosapiens* cerebral cell adhesion molecule mrna. | 0.6 |
| IPI00011194 | FGFBP2 | fibroblast growth factor-binding protein 2 precursor. | 0.6 |
| IPI00001610 | IGF1 | insulin-like growth factor ia precursor. | 0.6 |
| IPI00011832 | SPP2 | secreted phosphoprotein 24 precursor. | 0.5 |
| IPI00008603 | ACTA2 | actin, aortic smooth muscle. | 0.5 |
| IPI00232895 | DGAT2L6 | diacylglycerol o-acyltransferase 2-like protein 6. | 0.5 |
| IPI00550363 | TAGLN2 | transgelin-2. | 0.5 |
| IPI00020996 | IGFALS | insulin-like growth factor-binding protein complex acid labile chainprecursor. | 0.5 |
| IPI00550533 | MLLT11 | uncharacterized protein c1orf56. | 0.5 |
| IPI00292532 | CAMP | antibacterial protein fall-39 precursor. | 0.5 |
| IPI00019581 | F12 | coagulation factor xii precursor. | 0.5 |
| IPI00017530 | FCN2 | ficolin-2 precursor or LFicolin | 0.5 |
| IPI00385595 | TMPRSS12 | transmembrane protease, serine 12. | 0.5 |
| IPI00395667 | IFRD2 | interferon-related ifrd2 (pc4-b) protein. | 0.5 |
| IPI00027843 | PROZ | isoform 1 of vitamin k-dependent protein z precursor. | 0.5 |
| IPI00655976 | PRG4 | isoform c of proteoglycan-4 precursor. | 0.4 |
| IPI00301058 | VASP | vasodilator-stimulated phosphoprotein. | 0.4 |
| IPI00328748 | ARMET | armet protein precursor. | 0.4 |
| IPI00477597 | HPR | isoform 1 of haptoglobin-related protein precursor. | 0.4 |
| IPI00473014 | DSTN | destrin. | 0.4 |

TABLE 3-continued

Complete list of genes identified by MS-based proteomics in pooled plasma from SOS patients

| International Protein Index | Gene name | Gene Description | Ratio (mean) |
|---|---|---|---|
| IPI00102923 | FAM108A1 | protein fam108a1. | 0.4 |
| IPI00060181 | EFHD2 | ef-hand domain-containing protein 2, swiprosin-1 | 0.4 |
| IPI00302592 | FLNA | filamin a, alpha. | 0.4 |
| IPI00401283 | MEGF9 | multiple epidermal growth factor-like domains 9 precursor. | 0.4 |
| IPI00019848 | HCFC1 | isoform 1 of host cell factor. | 0.4 |
| IPI00022445 | PPBP | platelet basic protein precursor. | 0.4 |
| IPI00007750 | TUBA4A | tubulin alpha-1 chain. | 0.4 |
| IPI00335280 | RPE | isoform 1 of ribulose-phosphate 3-epimerase. | 0.4 |
| IPI00010414 | PDLIM1 | pdz and lim domain protein 1. | 0.4 |
| IPI00022731 | APOC4 | apolipoprotein c-iv precursor. | 0.4 |
| IPI00022295 | PF4V1 | platelet factor 4 variant precursor. | 0.4 |
| IPI00289876 | STX7 | isoform 1 of syntaxin-7. | 0.3 |
| IPI00017891 | APC2 | adenomatosis polyposis coli 2 protein. | 0.3 |
| IPI00009309 | CCL5 | small inducible cytokine a5 precursor. | 0.3 |
| IPI00253323 | ANKRD57 | ankyrin repeat domain-containing protein 57. | 0.3 |
| IPI00790010 | GULP1 | gulp, engulfment adaptor ptb domain containing 1. | 0.3 |
| IPI00168877 | HELB | helicase (dna) b. | 0.3 |
| IPI00022446 | PF4 | platelet factor 4 precursor. | 0.3 |
| IPI00217537 | ASXL1 | isoform 1 of putative polycomb group protein asxl1. | 0.3 |
| IPI00029193 | HGFAC | hepatocyte growth factor activator precursor. | 0.3 |
| IPI00746107 | TRIM35 | isoform 2 of tripartite motif-containing protein 35. | 0.3 |
| IPI00786924 | MFSD7 | similar to b0416.5a. | 0.3 |
| IPI00641826 | THOC6 | isoform 2 of the complex subunit 6 homolog. | 0.3 |
| IPI00179589 | MTPN | myotrophin. | 0.3 |
| IPI00185326 | FBXL10 | isoform 1 of jmjc domain-containing histone demethylation protein 1b. | 0.3 |
| IPI00010164 | C21orf91 | protein eurl homolog. | 0.3 |
| IPI00298994 | TLN1 | 271 kda protein. | 0.3 |
| IPI00794328 | TPD52 | 8 kda protein. | 0.3 |
| IPI00554497 | NHS | isoform 3 of nance-horan syndrome protein. | 0.3 |
| IPI00552243 | TMEM1/TRAPPC1 | hypothetical protein dkfzp667i0321 (fragment). | 0.3 |
| IPI00386763 | ADAMTS9 | isoform 1 of adamts-9 precursor. | 0.3 |
| IPI00008453 | CORO1C | coronin-1c. | 0.2 |
| IPI00155729 | PLXNB3 | plexin-b3 precursor. | 0.2 |
| IPI00334190 | STOML2 | stomatin-like protein 2. | 0.2 |
| IPI00292056 | PIK3C2B | phosphatidylinositol-4-phosphate 3-kinase c2 domain-containing betapolypeptide. | 0.2 |
| IPI00656092 | PRG4 | isoform f of proteoglycan-4 precursor. | 0.2 |
| IPI00017921 | BICC1 | isoform 2 of protein bicaudal c homolog 1. | 0.2 |
| IPI00008274 | CAP1 | adenylyl cyclase-associated protein 1. | 0.2 |
| IPI00292817 | KIAA1462 | novel protein. | 0.2 |
| IPI00022432 | TTR | transthyretin precursor. similar to calcium/calmodulin-dependent protein kinase type 1bki beta) (pregnancy upregulated non-ubiquitously expressed cam kinasehomolog). | 0.2 |
| IPI00550276 | PNCK | splice isoform 2. | 0.2 |
| IPI00164719 | KIAA1432 | protein kiaa1432. | 0.2 |
| IPI00329345 | SPATS2 | spats2 protein. | 0.2 |
| IPI00647939 | C6orf148 | cdna flj30329 fis, clone brace2007201. | 0.2 |
| IPI00783169 | F12 | coagulation factor xii. | 0.2 |
| IPI00019383 | GALK1 | galactokinase. | 0.1 |
| IPI00298347 | PTPN11 | isoform 2 of tyrosine-protein phosphatase non-receptor type 11. | 0.1 |
| IPI00299608 | PSMD1 | isoform 1 of 26s proteasome non-atpase regulatory subunit 1. | 0.1 |
| IPI00015983 | EDG3 | sphingosine 1-phosphate receptor edg-3. | 0.1 |
| IPI00442264 | ZNF195 | cdna flj16258 fis, clone hsyra2005628, moderately similar to zincfinger protein 195. | 0.1 |
| IPI00642639 | LAMA3 | 5 kda protein. | 0.1 |
| IPI00168627 | CXorf20 | uncharacterized protein cxorf20. | 0.1 |
| IPI00023456 | CHRM3 | muscarinic acetylcholine receptor m3. | 0.1 |
| IPI00480027 | KIAA0649 | 1a6/drim (down-regulated in metastasis) interacting protein. | 0.1 |
| IPI00646555 | ZNF452 | protein znf452. | 0.1 |
| IPI00027193 | CLIC5 | isoform 2 of chloride intracellular channel protein 5. | 0.1 |
| IPI00014287 | FOLR3 | folate receptor 3 precursor. | 0.0 |
| IPI00747210 | NBPF1 | conserved hypothetical protein. | 0.0 |
| IPI00032534 | GTPBP2 | 21 kda protein. | 0.0 |
| IPI00106882 | ZNF692 | isoform 1 of zinc finger protein 692. | 0.0 |

Example 2

In this Example, the biomarkers identified in Example 1 were further analyzed in plasma using sequential ELISAs from a validation set of 45 patients: 32 SOS patients at disease onset (days +14 to +21 post-HSCT) and from 13 time-matched controls.

The clinical characteristics of patients in this validation set are described in Table 1. Further, diagnosis samples from SOS+ patients that were taken at the time of SOS onset were used and samples from SOS− patients were selected so that both groups of samples were balanced according to time of acquisition. The clinical characteristics of patients in this training cohort are described in Table 1. The SOS− and SOS+ groups were balanced for age, primary disease, donor type (related versus unrelated), donor match, and intensity of the conditioning regimen (all full intensity with most receiving 16 mg/kg busulfan for 4 days or total body irradiation). More than 90% of patients received GVHD prophylaxis of methotrexate and tacrolimus (or cyclosporine) of standard duration. The value of these proteins as diagnostic biomarkers of SOS were analyzed using two-sample t-tests and by calculating the AUCs of the ROCs, which represent the false positive and true positive rates for every possible level of a marker.

Figure 3:
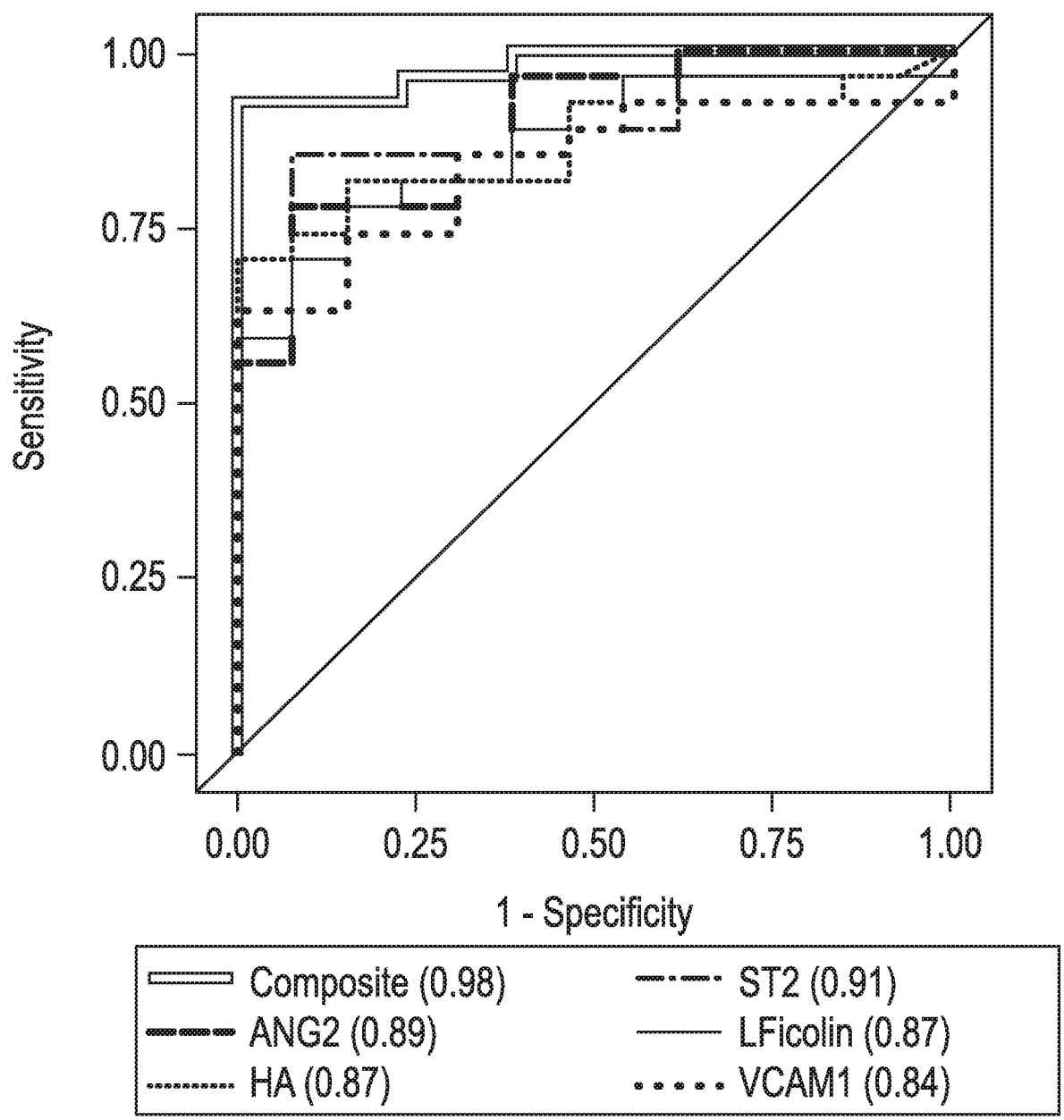
FIG. 3 depicts a composite ROC curve compared to the individual ROC curves for the five best SOS diagnostic markers (ST2, ANG2, L-Ficolin, HA, and VCAM1).

ST2, ANG2, L-Ficolin, HA, VCAM1, TIMP1, sCD141, ICAM1, and PAI-1 were identified as diagnostic biomarkers of SOS with p-values ranging from <0.001 to 0.04 and with AUCs between 0.91 and 0.70 (FIGS. 2A-2H). The composite ROC of markers ST2, ANG2, L-Ficolin, HA, and VCAM1 had an AUC of 0.98 (95% confidence interval, 0.94-1.00; FIG. 3). Addition of TIMP1, thrombomodulin, and ICAM1 to the biomarker panel did not improve this AUC value (data not shown). Because ST2 has been shown to correlate with the development of acute GVHD, its prognostic value in the training and independent cohorts was evaluated. In these 2 cohorts, approximately 45% of SOS patients later developed GVHD (median number of days to onset of 33 and 21 versus 11 and 9 for SOS in the training and independent cohorts, respectively). ST2 plasma concentrations at day 14 after HCT (when almost all SOS patients have already developed clinical signs of SOS) did not differ between the SOS+ GVHD− and SOS+ GVHD+ groups, meaning that for SOS cases, ST2 is a diagnostic marker of SOS and this is more important than its prognostic value for future GVHD.

Example 3

Figures 4A, 4B:
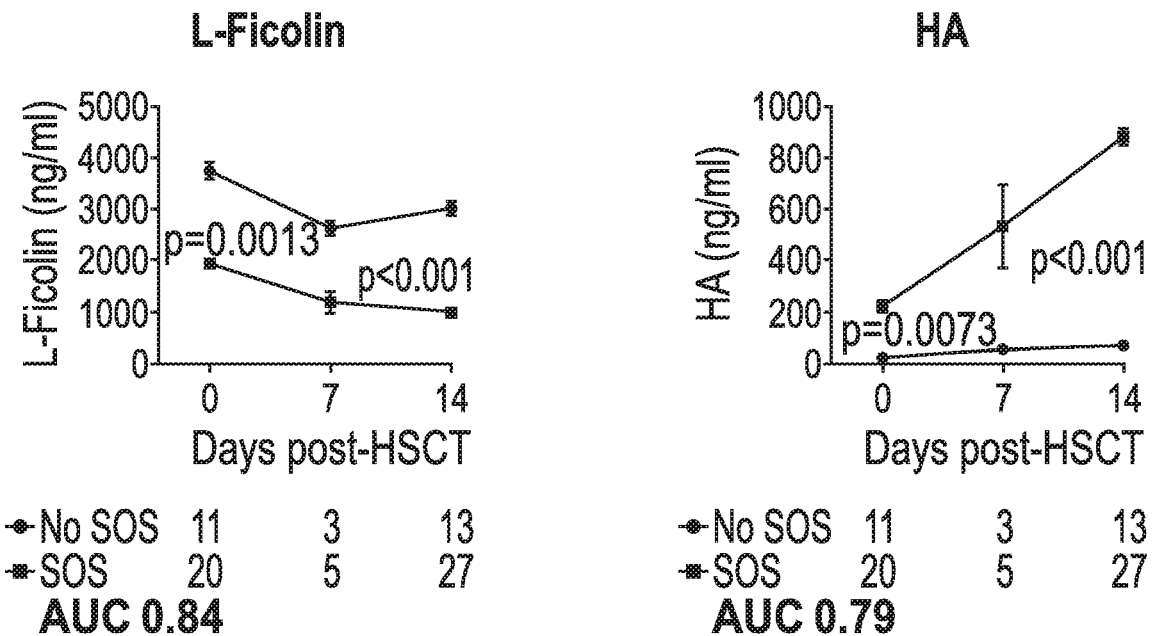
FIGS. 4A-4C depict curves for SOS markers measured at different times post-HSCT (0 days, 7 days, and SOS onset).
Figure 4C:
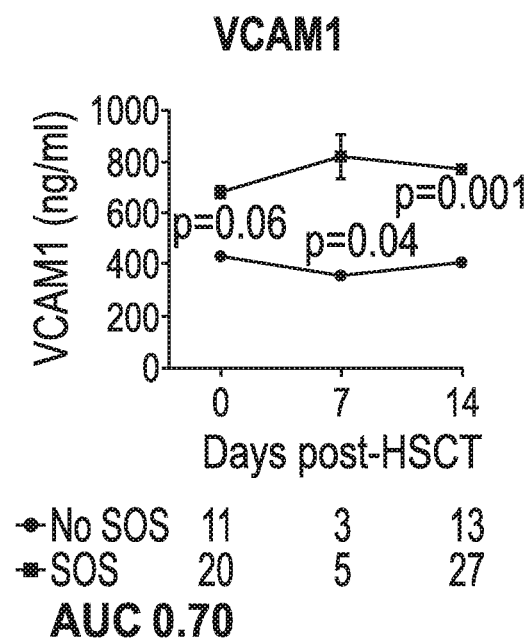
Figure 5A:
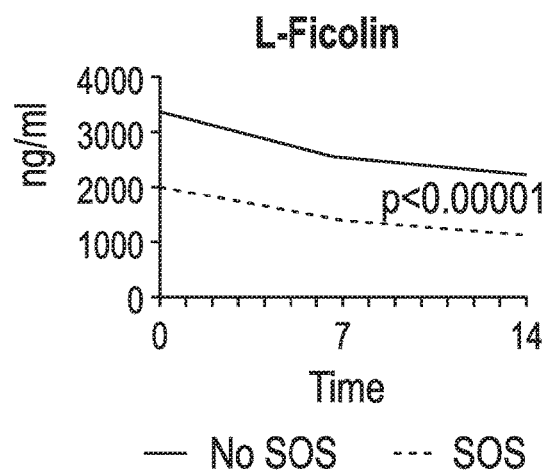
FIGS. 5A-5C depict the trajectories of L-Ficolin, HA, and VCAM1 in the training set as modeled by population mixed effects approach as analyzed in Example 3. Shown is the population median for each biomarker with the p-value comparing the trajectories of the two groups.
Figure 5B:
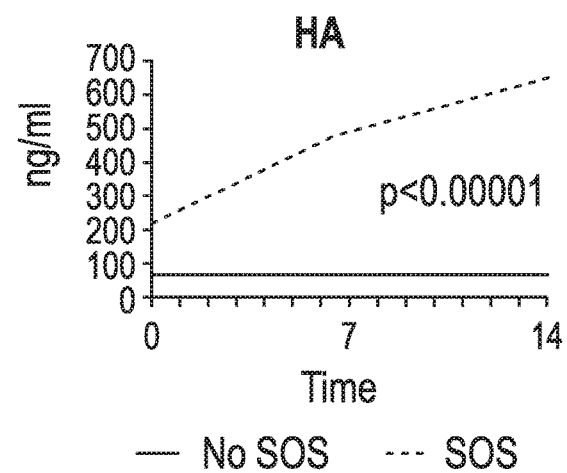
Figure 5C:
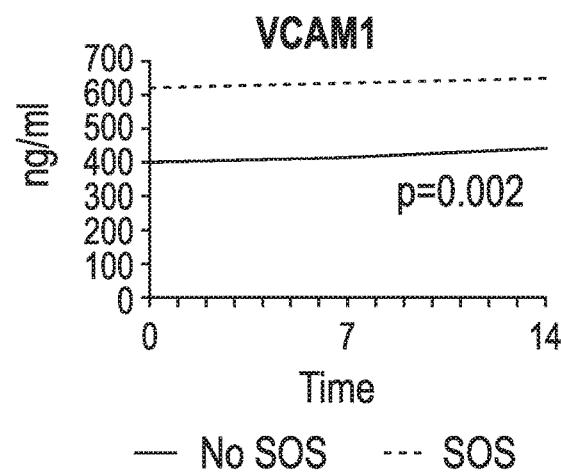

In this Example, the prognostic significance of the biomarkers identified in Example 2 was analyzed using Wicoxon Rank-Sum analysis of protein levels measured before presentation of the clinical signs (days 0 and +7 post-HSCT). Three diagnostic biomarkers were also determined to be prognostic before clinical signs were apparent (L-Ficolin, HA, and VCAM1; AUC: 0.83-0.69), and the corresponding AUC values for biomarker values on the day of HCT were between 0.84 and 0.70 (FIGS. 4A-4C). Modeling of these biomarkers' trajectories showed significant differences between the SOS− and SOS+ groups (FIGS. 5A-5C). These results indicated that biomarkers of innate immune response, mitochondrial clearance, and leukocyte-endothelial cell adhesion in the sinusoidal endothelial cells of the liver are altered prior to the clinical signs of SOS and can be detected as early as the day of HSCT (day 0).

Example 4

In this Example, three biomarkers (L-Ficolin, HA, and VCAM1) identified as prognostic biomarkers in Example 3 were validated as prognostic biomarkers in an independent set of 35 patients from the Indiana University HSCT biobank (13 patients with SOS; 22 patients without SOS). The prognostic significance of these biomarkers was analyzed using Wilcoxon Rank-Sum analysis of their plasma levels measured before the clinical signs (days 0, +7 post-HSCT, and +14 post-HSCT). Further, plasma levels of these markers measured pre-transplant showed no difference suggesting that the conditioning regimen (i.e., intense chemotherapy +/− total body irradiation to prepare the subject for its graft) explain the levels seen at day 0. Particularly, the conditioning regimen is conducted between day −7 (pre-sample (i.e., samples taken before the conditioning regimen)) and day −1. At day 0, the donor cells were injected before the graft was injected. Thus, the only difference between the day −7 and day 0 samples is the conditioning regimen.

Figures 6A, 6B:
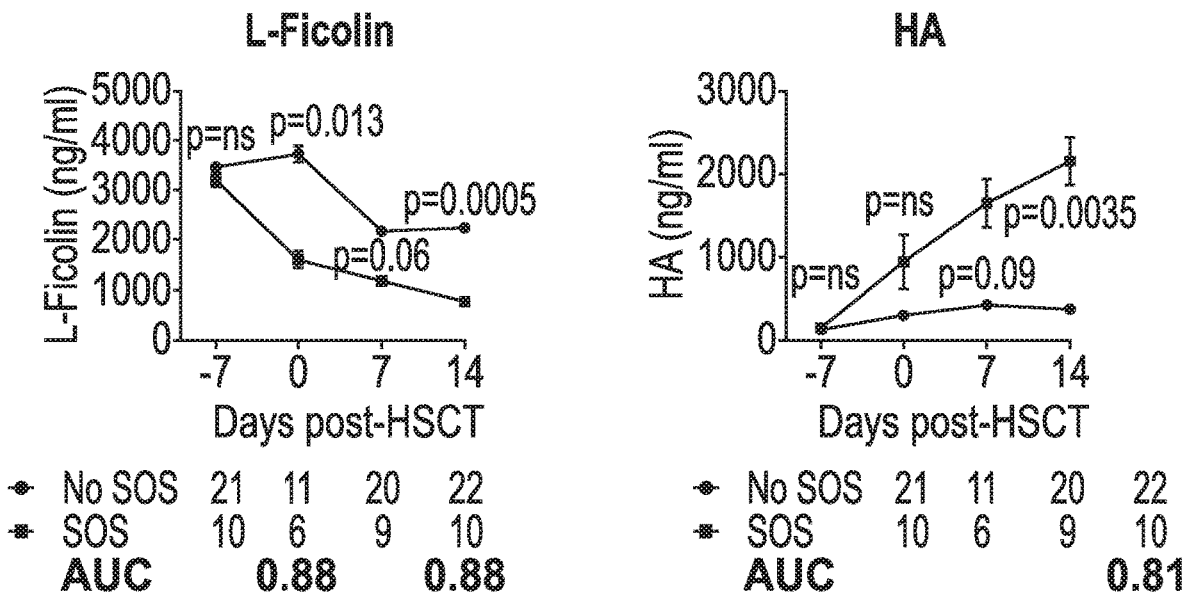
FIGS. 6A-6C depict curves for SOS markers measured at different times pre- and post-HSCT (−7 days, 0 days, 7 days, and 14 days). Shown is the population median for each biomarker with the p-value comparing the trajectories of the two groups.
Figure 6C:
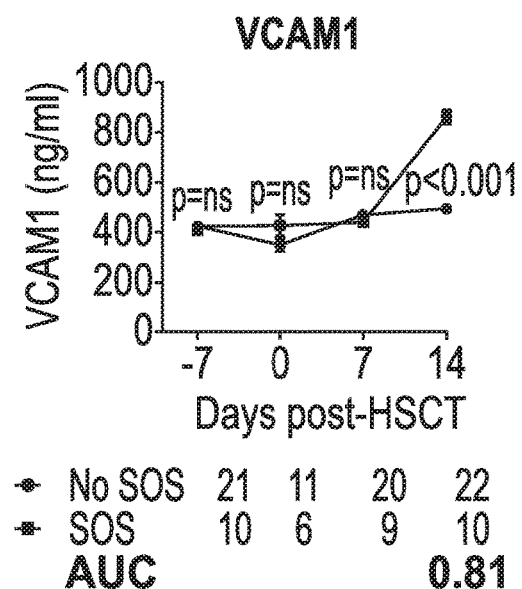

In this smaller set, L-Ficolin remained a strong prognosis marker as early as the day of transplant with an AUC of 0.88. Of note, the three markers were highly significant at day 14 (median day of onset) (see FIGS. 6A-6C).

Figure 7A:
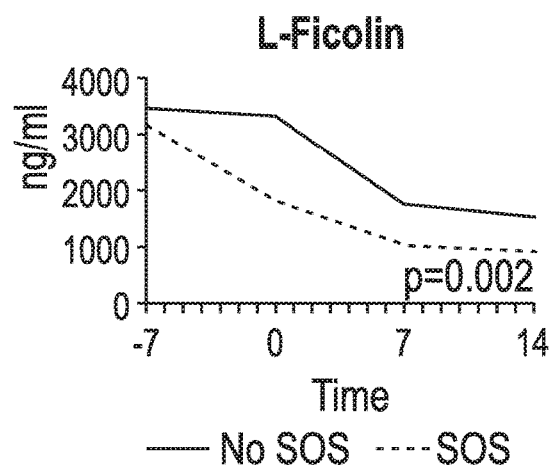
FIGS. 7A-7C depict the trajectories of L-Ficolin, HA, and VCAM1 in the independent set as modeled by population mixed effects approach as analyzed in Example 4. Shown is the population median for each biomarker with the p-value comparing the trajectories of the two groups.
Figure 7B:
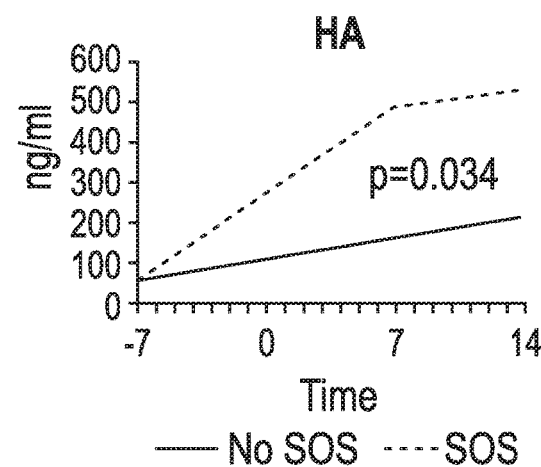
Figure 7C:
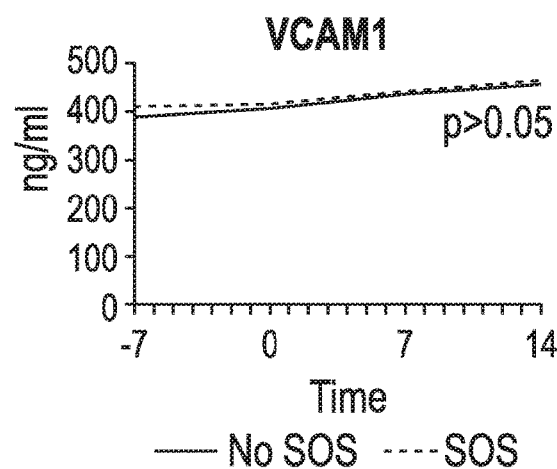

L-Ficolin, HA, and VCAM1 were then tested as prognostic markers of SOS with samples taken before the appearance of clinical signs of SOS. L-Ficolin and HA also stratified patients at risk for SOS as early as the day of HCT in this independent cohort (FIGS. 6A-6C. Modeling of these biomarkers trajectories showed significant differences between the SOS+ and SOS− groups for L-Ficolin and HA but not for VCAM1 (FIGS. 7A-7C). Notably, for most patients in this cohort, in addition to the day 0 and day 7 samples, samples collected before the conditioning were included, and plasma levels of L-Ficolin, and HA measured before transplantation did not differ between the SOS− and SOS+ groups. Therefore, these results strongly suggest that levels of these biomarkers are altered during the conditioning regimen and before the appearance of clinical signs of SOS, as they can be detected as early as the day of HCT.

Example 5

In this Example, a Naïve Bayes classifier implemented in Waikato Environment for Knowledge Analysis (WEKA) was developed for SOS prognosis based on a balanced subset of 24 patients (11 SOS−; 13 SOS+). The classifier performance was evaluated by doing a 10-fold cross-validation.

Naïve Bayes is an algorithm that is based on Bayes rule of probability. It combines all attributes to maximize the probability of a correct prediction for an outcome. It works by calculating the probabilities for each attribute and then multiplying them.

Infogain is an attribute selection algorithm that evaluates each attribute separately by calculating their information gain with respect to the outcome.

10-fold Cross-Validation: a technique that partitions the dataset into 10-folds. Each fold is held out for testing or validating the model and the remainder is used for learning or building the model.

Figure 8:
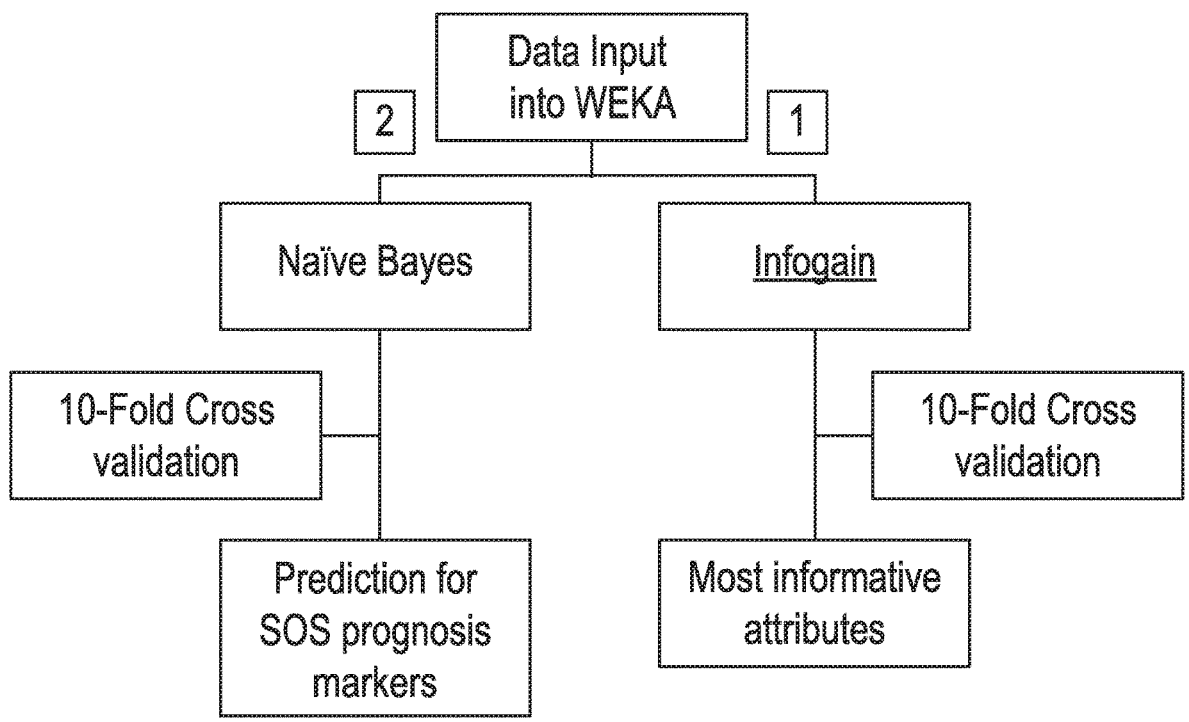
FIG. 8 depicts the modeling strategy for SOS prognosis as used in Example 5.

The modeling strategy used both models (see FIG. 8):
1) The infogain algorithm with 10-fold cross-validation that resulted in the selection of the most informative attributes.
2) The Naïve Bayes model with 10-fold cross-validation that resulted in the generation of the final prediction.

The attributes tested were:
1) VCAM-1, L-Ficolin, HA (day 0 and slope)
2) Age at SOS Onset 3) Gender
4) Donor Type (RD, URD)
5) Match (yes, no)
6) Transplant Period (<2005=0, >2005=1)
7) Transplant number out of total transplantation (one=0, more than one=1)
8) Conditioning Regimen:
   a. TBI inclusion
   b. Busulfan inclusion
   c. Cyclophosphamide inclusion Three different groups of patients were evaluated:
1) Subset 1 was an imbalanced dataset (8 SOS− versus 20 SOS+) that included some missing day 0 biomarker information,
2) Subset 2 was a balanced dataset (11 SOS− versus 13 SOS+) that included complete clinical and biomarker information, and
3) subset 3 was a balanced dataset (21 SOS− versus 20 SOS+) that included some missing day 0 biomarker information.

The balanced subset 2 with no missing attribute information was selected to build the prognostic model. This selection was based on results comparing the correct prognosis between the 3 subsets tested and their corresponding ROC AUCs (Table 4).

TABLE 4

Naïve Bayes classifier results stratified
by 10-fold cross-validation (subset comparison)

|  | Subset One* (n = 28) | Subset Two** (n = 24) | Subset Three*** N = 42) |
|---|---|---|---|
| Correct Prediction | 71.43% | 83.33% | 73.17% |
| ROC AUC (Yes) | 0.856 | 0.902 | 0.831 |
| False Positive | 1 | 1 | 2 |
| False Negative | 7 | 3 | 9 |

*Dataset was imbalanced (8 SOS− vs 20 SOS+). Includes some missing biomarker day 0 plasma concentrations.
**Dataset was balanced (11 SOS− vs 13 SOS+). Attribute information is complete (i.e., no missing data for any attribute).

The clinical characteristics of patients in this set are presented in Table 5.

TABLE 5

Clinical characteristics of patients
in the Bayesian model development set

| Characteristic |  | SOS− (n = 11) | SOS+ (n = 13) |
|---|---|---|---|
| Age, years | Median | 49 | 14 |
|  | Range | 3-55 | 2-58 |
| Gender | Male | 5(45) | 10(77) |
|  | Female | 6(55) | 3(23) |
| Transplantation period, n (%) | 2005 or before | 8(73) | 9(69) |
|  | After 2005 | 3(27) | 4(31) |
| Transplantation number, n (%) | 1 | 10(91) | 11(85) |
|  | >1 | 1(9) | 2(15) |
| Donor type, n (%) | Related/Auto | 10(91) | 8(62) |
|  | Unrelated | 1(9) | 5(38) |
| Donor match, n (%) | Matched/Auto | 11(100) | 9(69) |
|  | Mismatched | 0(0) | 4(31) |
| Conditioning regimen type, n (%) | Chemotherapy only | 9(82) | 11(85) |
|  | Chemotherapy + TBI | 2(18) | 2(15) |
| Busulfan in conditioning regimen, n (%) | Yes | 9(82) | 10(77) |
|  | No | 2(18) | 3(23) |
| Cyclophosphamide in conditioning regimen, n (%) | Yes | 9(82) | 11(85) |
|  | No | 2(18) | 2(15) |

The model was evaluated using plasma concentrations of biomarkers on day 0 with and without the addition of the clinical characteristics. Table 6 shows the results (correct prognosis and false negatives and positives) of the model building using the selected data subset. The correct prognosis was achieved in 83.3% of patients using the day 0 plasma biomarker concentrations in addition to clinical attributes (ROC AUC=0.90).

TABLE 6

Naïve Bayes Classifier Results
Stratified by Ten-fold Cross-Validation

|  | Clinical Characteristics + Biomarkers | Biomarkers | Clinical Characteristics |
|---|---|---|---|
| Correct prognosis | 83.3% | 70.8% | 58.3% |
| ROC AUC (yes) | .90 | .83 | .61 |
| False positive | 1 | 1 | 4 |
| False negative | 3 | 6 | 6 |

The results of the infogain (Table 7) showed that in all groups the biomarkers at day 0 or the biomarker slopes provided the best infogain.

TABLE 7

Infogain

| Unbalanced (with missing values, only validation set) | Balanced (no missing values, only validation set) | Balanced (validation and independent sets) |
|---|---|---|
| L-Ficolin imputed day 0 | HA slope | HA slope |
| L-Ficolin day 0 | HA day 0 | L-Ficolin imputed day 0 |
| VCAM-1 day 0 | VCAM-1 day 0 | HA day 0 |
| HA slope | L-Ficolin day 0 | L-Ficolin day 0 |
| HA imputed day 0 | VCAM-1 slope | VCAM-1 day 0 |
| HA day 0 | Match | Match |
| Match | Donor type | Donor type |
| BU in CONREG | Gender | CONREG |
| Transplantation number | Transplantation number | BU in CONREG |
| Donor type | BU in CONREG | Transplantation period |
| Gender | CY in CONREG | Gender |
| CONREG | CONREG | Transplantation number |
| CY in CONREG | Transplantation period | CY in CONREG |
| Transplantation period |  | Age at BMT |

Example 6

In this Example, the diagnostic and prognostic values of the biomarkers were analyzed in an independent prospective set of 16 patients from the Indiana University HSCT biobank (6 patients with SOS; 10 patients without SOS). The basic and clinical characteristics of patients in this independent set are presented in Table 8. Despite the small sample size, the results further validated L-Ficolin and HA as diagnostic (AUC: 0.83 and 0.75, respectively) and prognostic markers of SOS.

TABLE 8

Clinical characteristics of patients in the independent set

| Characteristic | | SOS−<br>(N = 10) | SOS+<br>(N = 6) | P |
|---|---|---|---|---|
| Age, years | Median | 37 | 5 | 0.06 |
| | Range | 1-66 | 1-19 | |
| Disease, n (%) | Malignant* | 10 (100) | 6 (100) | ns |
| | Non-malignant§ | 0 (0) | 0 (0) | |
| Donor type, n (%) | Related/Auto | 8 (80) | 3 (50) | ns |
| | Unrelated/Cord | 2 (20) | 3 (50) | |
| Donor match, n (%) | Matched/Auto | 10 (100) | 4 (66) | ns |
| | Mismatched | 0 (0) | 2 (34) | |
| Conditioning regimen intensity, n (%) | Full‡ | 10 (100) | 6 (100) | ns |
| | With Busulfan | 0 (0) | 2 (34) | |
| | With TBI | 0 (0) | 2 (34) | |
| SOS onset day | Median | na | 11 | na |
| | Range | na | 7-23 | |
| Sample day post-HSCT | Median | 14 | 11 | ns |
| | Range | na | 7-23 | | na: not applicable,
ns: not significant
*Malignant disease includes acute leukemia/MDS (n = 7), lymphoma (n = 1), chronic leukemia (n = 1), neuroblastoma (n = 3), rhabdoid tumor (n = 1) and carcinoid tumor (n = 1)
‡Full-Intensity conditioning regimens include: BuCy (n = 1), BAC (n = 15), CyTBI (n = 2), FluBu (n = 1), Fludarabine/Melphalan (n = 1), Carboplatin/Etoposide/Melphalan (n = 4), Carboplatin/Thiotepa (n = 2), CyFlu (n = 4), and CyThiotepa (n = 2)

Based on the foregoing Examples, for the first time, biomarkers of SOS in plasma samples from patients undergoing allogeneic HSCT were identified. In addition to identifying a panel of biomarkers that can be used for SOS diagnosis (i.e., together ST2, ANG2, L-Ficolin, HA, and VCAM1 represent a biomarker panel for reliable, non-invasive diagnosis of SOS (AUC=0.98)), a panel of three biomarkers (L-Ficolin, HA, and VCAM1) were identified that can be used to evaluate the risk of developing SOS before clinical signs appear, even as early as the day of HSCT. L-Ficolin, HA, and VCAM1 can stratify patients at risk of SOS as early as the day of HSCT, which has therapeutic consequences including potential preemptive interventions. L-Ficolin's mechanism of action implicates pathways in SOS other than those related to hemostasis and endothelial injury.

These results demonstrate that SOS can be diagnosed based on a panel of biomarkers in plasma as well as predicted as early as the day of HSC infusion in patients. The identified markers represent several pathways, including pathways suspected to be involved in hemostasis and endothelial injury, as well as novel pathways related to innate immunity and homeostatic clearance of mitochondria. Analyses using the biomarker panels provide preemptive intervention to minimize the incidence and severity of SOS clinical symptoms, and thereby increase survival.

Bayesian Modeling Discussion

Bayesian modeling infers causal relationships between molecular interactions by randomly generating many possible network models and using statistical techniques to select a consensus model that best fits the data. Thus, these methods balance the trade-off between prior knowledge and the data. A Bayesian model was developed to confirm the value of the prognostic biomarker panels to risk-stratify the patients for SOS with a more unbiased approach. The high sensitivity and specificity of the biomarkers identified in the present disclosure make them useful for real-time clinical testing and early clinical intervention.

Figure 9:
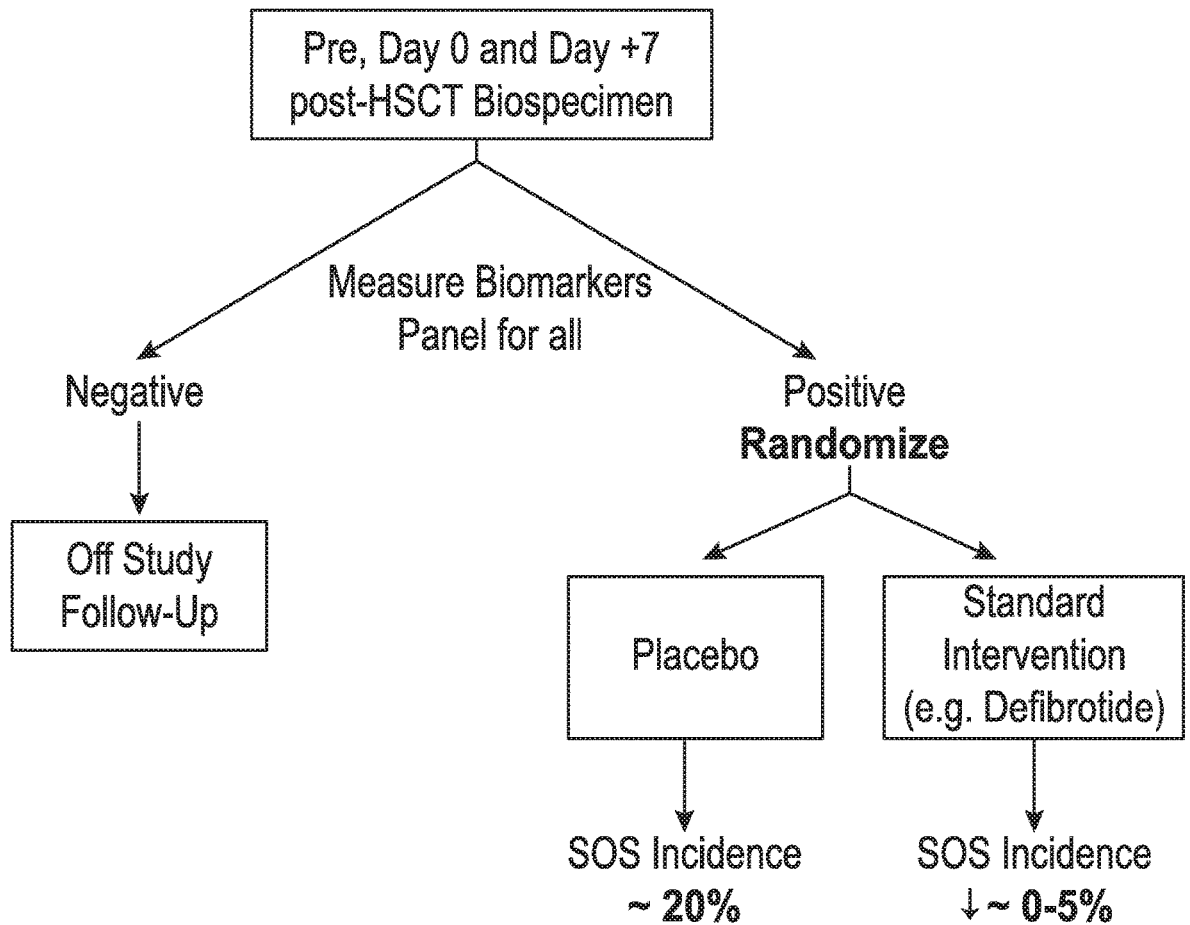
FIG. 9 depicts a preemptive SOS trial based on prognostic biomarker model.

A proposed SOS preemptive clinical study is presented in FIG. 9. Biomarker cutoffs can be used to risk-stratify patients at low- or high-risk for developing SOS before presentation of the clinical signs. Low-risk patients will receive no preemptive intervention, whereas high-risk patients will be randomized to receive either a standard SOS intervention (defibrotide) or no intervention. A comparison of outcomes from the randomized high-risk groups will show whether the preemptive intervention reduces the incidence of SOS in high-risk patients identified according to the developed biomarker panel. The expectation is that subclinical SOS can be effectively managed via early treatment.

What is claimed is:

1. A method of detecting the presence of proteins L-Ficolin, hyaluronic acid (HA), and IL-1RL1 (ST2) that constitute a biomarker panel, in a subject receiving hematopoietic cell transplantation (HCT), the method comprising:
    providing a biological sample from the subject;
    contacting the biological sample obtained from the subject with (i) a first agent that specifically binds to L-Ficolin and forms a first agent-biomarker complex; (ii) a second agent that specifically binds to HA and forms a second agent-biomarker complex; and (iii) a third agent that specifically binds to IL-1RL1 (ST2) and forms a third agent-biomarker complex; and
    detecting the formation of each first, second and third agent-biomarker complexes, thereby determining the presence of the biomarker panel in said biological sample.

2. The method of claim 1 further comprising contacting the biological sample obtained from the subject with a fourth agent that specifically binds to VCAM1 and forms a fourth agent-biomarker complex; and detecting the formation of the fourth-agent biomarker complex in the biological sample.

3. The method of claim 2 wherein the fourth agent is an antibody.

4. The method of claim 1 wherein the first, second and third agents are antibodies.

5. A method of treating sinusoidal obstructive syndrome (SOS) in a subject receiving hematopoietic stem cell transplantation (HSCT), said the method comprising
    identifying a patient at risk SOS by
        obtaining a biological sample from a subject receiving HSCT;
        measuring in said biological sample from the subject the expression of at least three biomarkers selected from the group consisting of L-Ficolin, hyaluronic acid (HA) IL-1RL1 (ST2), and VCAM1 by contacting the biological sample obtained from the subject with specific binding agents that specifically bind to each of the respective the biomarkers, wherein the each specific binding agent forms a complex with the respective biomarker; and
        detecting the agent-biomarker complexes, thereby determining the biomarker expression level; wherein an elevated biomarker expression level of said at least three biomarkers compared to biomarker expression obtained from a biological sample obtained from a control is indicative of SOS; and
    treating said patient at risk of SOS with defibrotide.

6. A method of treating sinusoidal obstructive syndrome (SOS) in a subject receiving hematopoietic stem cell transplantation (HSCT), said method comprising:

administering defibrotide to a subject identified as being in need of treatment, wherein said subject identified as being in need of treatment for SOS has an elevated biomarker expression level of at least three biomarkers selected from the group consisting of L-Ficolin, hyaluronic acid (HA), IL-1RL1 (ST2), and VCAM1, relative to the corresponding biomarker expression obtained from a control.

* * * * *